(12) United States Patent
Chan et al.

(10) Patent No.: US 10,736,957 B2
(45) Date of Patent: Aug. 11, 2020

(54) ENHANCED IMMUNOGENICITY OF MRNA WITH CO-ENCODED ADJUVANT SEQUENCES

(71) Applicant: PRESIDENT AND FELLOWS OF HARVARD COLLEGE, Cambridge, MA (US)

(72) Inventors: Ying Kai Chan, Cambridge, MA (US); Jessica Jing-Shiuan Chiang, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/152,096

(22) Filed: Oct. 4, 2018

(65) Prior Publication Data

US 2019/0184006 A1 Jun. 20, 2019

Related U.S. Application Data

(60) Provisional application No. 62/607,480, filed on Dec. 19, 2017, provisional application No. 62/665,203, filed on May 1, 2018, provisional application No. 62/670,320, filed on May 11, 2018.

(51) Int. Cl.
| | |
|---|---|
| *A61K 39/12* | (2006.01) |
| *A61K 39/145* | (2006.01) |
| *C12N 15/117* | (2010.01) |
| *A61K 39/39* | (2006.01) |
| *A61P 31/16* | (2006.01) |
| *A61K 39/00* | (2006.01) |

(52) U.S. Cl.
CPC ............ *A61K 39/145* (2013.01); *A61K 39/12* (2013.01); *A61K 39/39* (2013.01); *A61P 31/16* (2018.01); *C12N 15/117* (2013.01); *A61K 2039/51* (2013.01); *A61K 2039/53* (2013.01); *A61K 2039/55561* (2013.01); *C12N 2310/17* (2013.01); *C12N 2310/3519* (2013.01); *C12N 2760/16134* (2013.01)

(58) Field of Classification Search
None
See application file for complete search history.

(56) References Cited

U.S. PATENT DOCUMENTS

| | | |
|---|---|---|
| 2012/0177701 A1 | 7/2012 | Ilyinskii et al. |
| 2016/0000848 A1 | 1/2016 | Koganov et al. |
| 2017/0196969 A1 | 7/2017 | Kallen et al. |
| 2017/0266268 A1 | 9/2017 | Kallen et al. |

FOREIGN PATENT DOCUMENTS

| | | | |
|---|---|---|---|
| WO | 2012/113513 A1 | 8/2012 | |
| WO | WO-2016179034 A2 * | 11/2016 | ............ A61P 31/14 |
| WO | 2017162461 A1 | 9/2017 | |
| WO | 2017214378 A1 | 12/2017 | |
| WO | 2018172546 A1 | 9/2018 | |

OTHER PUBLICATIONS

Chow et al., "PRRs are watching you: Localization of innate sensing and signaling regulators." Virology 479-480:104-109 (2015).
Heidenreich et al., "A novel RNA-based adjuvant combines strong immunostimulatory capacities with a favorable safety profile." International Journal of Cancer 137(2):372-384 (2015).
Iwasaki et al., "Regulation of adaptive immunity by the innate immune system." Science 327(5963):291-295 (2010).
Luo et al., "Structural insights into RNA recognition by RIG-I" Cell 147(2): 1-23 (2011).
Saito et al., "Innate Immunity Induced by Composition-Dependent RIG-I Recognition of Hepatitis C Virus RNA" Nature 454(7203): 1-10 (2008).
Schmidt et al., "5'-Triphosphate RNA Requires Base-Paired Structures to Activate Antiviral Signaling via RIG-I." Proceedings of the National Academy of Sciences of the United States of America 106(29): 12067-12072 (2009).

* cited by examiner

*Primary Examiner* — J. E Angell
(74) *Attorney, Agent, or Firm* — Nixon Peabody LLP; David S. Resnick; Mark J. FitzGerald

(57) ABSTRACT

Described herein are in vitro-transcribed (IVT) RNA molecules comprising, a 5' cap structure, a coding region encoding an antigen polypeptide, an immunostimulatory RNA sequence, and a poly(A) tail.

13 Claims, 5 Drawing Sheets

Specification includes a Sequence Listing.

A pUUC: 5'-GGCCAUCCUGUUUUUUCCCUUUUUUUUUCUUUUUUUUUU
UUUUUUUUUUUUUUUUUUUUCUCCUUUUUUUUUCCUCUUUUUU
CCUUUUCUUCCUUU-3'

DVG: 5'-UGUCAUAUGGAUAAGUCCAAGACUAUCUUUAUCUAUGUCCACAA-3'

B

SEQUENCE LISTING

```
<160> NUMBER OF SEQ ID NOS: 90

<210> SEQ ID NO 1
<211> LENGTH: 104
<212> TYPE: RNA
<213> ORGANISM: Hepatitis C virus

<400> SEQUENCE: 1
ggccauccug uuuuuuuccc uuuuuuuuuu ucuuuuuuuu uuuuuuuuuu uuuuuuuuuu     60
uuuuuucucc uuuuuuuuuc cucuuuuuuu ccuuuucuuc cuuu                    104

<210> SEQ ID NO 2
<211> LENGTH: 44
<212> TYPE: RNA
<213> ORGANISM: Sendai virus

<400> SEQUENCE: 2
ugucauaugg auaaguccaa gacuaucuuu aucuaugucc acaa                     44

<210> SEQ ID NO 3
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(40)
<223> OTHER INFORMATION: g, u, an analogue of g or an analogue of u
<220> FEATURE:
<221> NAME/KEY: modified_base
<222> LOCATION: (41)..(43)
<223> OTHER INFORMATION: g, u, a, t, c or an analogue of g, u, a, t or c
<220> FEATURE:
<221> NAME/KEY: modified_base
```

```
<222> LOCATION: (44)..(83)
<223> OTHER INFORMATION: g, u, an analogue of g or an analogue of u
<220> FEATURE:
<223> OTHER INFORMATION: See specification as filed for detailed
      description of substitutions and preferred embodiments

<400> SEQUENCE: 3
nnnnnnnnnn nnnnnnnnnn nnnnnnnnnn nnnnnnnnnn nnnnnnnnnn nnnnnnnnnn        60
nnnnnnnnnn nnnnnnnnnn nnn                                                 83

<210> SEQ ID NO 4
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(40)
<223> OTHER INFORMATION: c, u, an analogue of c or an analogue of u
<220> FEATURE:
<221> NAME/KEY: modified_base
<222> LOCATION: (41)..(43)
<223> OTHER INFORMATION: g, u, a, t, c or an analogue of g, u, a, t or c
<220> FEATURE:
<221> NAME/KEY: modified_base
<222> LOCATION: (44)..(83)
<223> OTHER INFORMATION: c, u, an analogue of c or an analogue of u
<220> FEATURE:
<223> OTHER INFORMATION: See specification as filed for detailed
      description of substitutions and preferred embodiments

<400> SEQUENCE: 4
nnnnnnnnnn nnnnnnnnnn nnnnnnnnnn nnnnnnnnnn nnnnnnnnnn nnnnnnnnnn        60
nnnnnnnnnn nnnnnnnnnn nnn                                                 83

<210> SEQ ID NO 5
<211> LENGTH: 5083
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2500)
<223> OTHER INFORMATION: g, u, a, t, c or an analogue of g, u, a, t or c
<220> FEATURE:
<221> NAME/KEY: misc_feature
<222> LOCATION: (1)..(2500)
<223> OTHER INFORMATION: This region may encompass 0-50 repeats of a
      sequence 4-50 nucleotides in length, wherein some positions or the
      entire region may be absent
<220> FEATURE:
<221> NAME/KEY: modified_base
<222> LOCATION: (2501)..(2540)
<223> OTHER INFORMATION: g, u, an analogue of g or an analogue of u
<220> FEATURE:
<221> NAME/KEY: modified_base
<222> LOCATION: (2541)..(2543)
<223> OTHER INFORMATION: g, u, a, t, c or an analogue of g, u, a, t or c
<220> FEATURE:
<221> NAME/KEY: modified_base
<222> LOCATION: (2544)..(2583)
<223> OTHER INFORMATION: g, u, an analogue of g or an analogue of u
<220> FEATURE:
```

<221> NAME/KEY: modified_base
<222> LOCATION: (2584)..(5083)
<223> OTHER INFORMATION: g, u, a, t, c or an analogue of g, u, a, t or c
<220> FEATURE:
<221> NAME/KEY: misc_feature
<222> LOCATION: (2584)..(5083)
<223> OTHER INFORMATION: This region may encompass 0-50 repeats of a
      sequence 4-50 nucleotides in length, wherein some positions or the
      entire region may be absent
<220> FEATURE:
<223> OTHER INFORMATION: See specification as filed for detailed
      description of substitutions and preferred embodiments

<400> SEQUENCE: 5

```
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
```

| | |
|---|---|
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |
| nnnnnnnnnn nnnnnnnnnn nnnnnnnnnn nnnnnnnnnn nnnnnnnnnn nnnnnnnnnn | 3420 |
| nnnnnnnnnn nnnnnnnnnn nnnnnnnnnn nnnnnnnnnn nnnnnnnnnn nnnnnnnnnn | 3480 |
| nnnnnnnnnn nnnnnnnnnn nnnnnnnnnn nnnnnnnnnn nnnnnnnnnn nnnnnnnnnn | 3540 |
| nnnnnnnnnn nnnnnnnnnn nnnnnnnnnn nnnnnnnnnn nnnnnnnnnn nnnnnnnnnn | 3600 |
| nnnnnnnnnn nnnnnnnnnn nnnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |
| nnnnnnnnnn nnnnnnnnnn nnnnnnnnnn nnnnnnnnnn nnnnnnnnnn nnnnnnnnnn | 4080 |
| nnnnnnnnnn nnnnnnnnnn nnnnnnnnnn nnnnnnnnnn nnnnnnnnnn nnnnnnnnnn | 4140 |
| nnnnnnnnnn nnnnnnnnnn nnnnnnnnnn nnnnnnnnnn nnnnnnnnnn nnnnnnnnnn | 4200 |
| nnnnnnnnnn nnnnnnnnnn nnnnnnnnnn nnnnnnnnnn nnnnnnnnnn nnnnnnnnnn | 4260 |
| nnnnnnnnnn nnnnnnnnnn nnnnnnnnnn nnnnnnnnnn nnnnnnnnnn nnnnnnnnnn | 4320 |

```
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnn                      5083

<210> SEQ ID NO 6
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6 aaaaa                                                                    5

<210> SEQ ID NO 7
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gaagcaaucu ccacuuacua gaaa                                              24

<210> SEQ ID NO 8
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggacguacgu uucgacguac gucc                                              24

<210> SEQ ID NO 9
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggacguacgu uucgacguac gucc                                              24
```

```
<210> SEQ ID NO 10
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaucgaucg aucguucgcg aucgaucgau cc                                    32

<210> SEQ ID NO 11
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ggaucgaucg aucguucgcg aucgaucgau cc                                    32

<210> SEQ ID NO 12
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggaucgaucg aucguucgcg aucgaucgau cc                                    32

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gcaugcgacc ucuguuuga                                                   19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ucaaacagag gucgcaugc                                                   19

<210> SEQ ID NO 15
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aacacacaca cacacacaca cuuu                                             24
```

```
<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gugugugugu gugugugugu u                                              21

<210> SEQ ID NO 17
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aacacacaca cacacacaca cuuu                                           24

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aagugugugu gugugugugu guu                                            23

<210> SEQ ID NO 19
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggacguacgu uucgcgacug uaga                                           24

<210> SEQ ID NO 20
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ucuacagucg cgaaacguac gucc                                           24

<210> SEQ ID NO 21
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggacguacgu uucgcgacug uaga                                           24

<210> SEQ ID NO 22
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucuacagucg cgaaacguac gucc                                          24

<210> SEQ ID NO 23
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: U or a derivative thereof
<220> FEATURE:
<223> OTHER INFORMATION: See specification as filed for detailed
      description of substitutions and preferred embodiments

<400> SEQUENCE: 23 vumm                                                                 4

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
acccaucuau uauauaacuc                                               20

<210> SEQ ID NO 25
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25 auaggcac                                                             8

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gccaccgagc cgaauauac                                                19

<210> SEQ ID NO 27
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 27
auauauauau auauauauau                                              20

<210> SEQ ID NO 28
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uuauuauuau uauuauuauu                                              20

<210> SEQ ID NO 29
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aauaauaaua auaauaauaa                                              20

<210> SEQ ID NO 30
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aaauaaauaa auaaauaaau                                              20

<210> SEQ ID NO 31
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aaaauaaaau aaaauaaaau                                              20

<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cuacuacuac uacuacuacu                                              20

<210> SEQ ID NO 33
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
``` uuauuau                                                                    7

<210> SEQ ID NO 34
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34 uauauau                                                                    7

<210> SEQ ID NO 35
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ccgagccgca uuaccc                                                         16

<210> SEQ ID NO 36
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ccgagccgau ugaacc                                                         16

<210> SEQ ID NO 37
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ccgagccgaa uacccc                                                         16

<210> SEQ ID NO 38
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccgagccaua uauauc                                                         16

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ccgagccgau auuacc                             16

<210> SEQ ID NO 40
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ccgagccgaa uccccc                             16

<210> SEQ ID NO 41
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ccgagccgcc uacccc                             16

<210> SEQ ID NO 42
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ccgagccaua uauccc                             16

<210> SEQ ID NO 43
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ccgagccgcu auaccc                             16

<210> SEQ ID NO 44
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgagccgaa uaaccc                             16

<210> SEQ ID NO 45
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ccgagccgcu auccccc                            16

<210> SEQ ID NO 46
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ccgagccgaa gguacc                                                    16

<210> SEQ ID NO 47
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ccgagccgaa gauacc                                                    16

<210> SEQ ID NO 48
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ccgagccgaa uguacc                                                    16

<210> SEQ ID NO 49
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ccgagccgcc uaaccc                                                    16

<210> SEQ ID NO 50
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ccgagccgca uauccc                                                    16

<210> SEQ ID NO 51
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ccgagccgaa gcuacc                                                    16

```
<210> SEQ ID NO 52
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ccgagccgca uacccc                                                       16

<210> SEQ ID NO 53
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ccgagccgca uaaccc                                                       16

<210> SEQ ID NO 54
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ccgagccgaa ggugcc                                                       16

<210> SEQ ID NO 55
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ccgagccgca uccccc                                                       16

<210> SEQ ID NO 56
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ccgagccgaa gcugcc                                                       16

<210> SEQ ID NO 57
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ccgagccgcc gccccc                                                       16
```

```
<210> SEQ ID NO 58
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ccgagccgaa gcuccc                                                       16

<210> SEQ ID NO 59
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ccgagccgaa ggcacc                                                       16

<210> SEQ ID NO 60
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60 yuku                                                                     4

<210> SEQ ID NO 61
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61 rurgy                                                                    5

<210> SEQ ID NO 62
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62 guugb                                                                    5

<210> SEQ ID NO 63
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63 guguk                                                                    5

<210> SEQ ID NO 64
```

```
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64 sumggcac                                                                  8

<210> SEQ ID NO 65
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65 cugu                                                                      4

<210> SEQ ID NO 66
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66 cuuu                                                                      4

<210> SEQ ID NO 67
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67 uugu                                                                      4

<210> SEQ ID NO 68
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68 uuuu                                                                      4

<210> SEQ ID NO 69
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69 guagu                                                                     5

<210> SEQ ID NO 70
<211> LENGTH: 5
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70 guagc                                                                      5

<210> SEQ ID NO 71
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71 guggu                                                                      5

<210> SEQ ID NO 72
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72 guggc                                                                      5

<210> SEQ ID NO 73
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73 auagu                                                                      5

<210> SEQ ID NO 74
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74 auagc                                                                      5

<210> SEQ ID NO 75
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75 auggu                                                                      5

<210> SEQ ID NO 76
<211> LENGTH: 5
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 76 auggc                                                                    5

<210> SEQ ID NO 77
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77 guagugu                                                                  7

<210> SEQ ID NO 78
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78 guugu                                                                    5

<210> SEQ ID NO 79
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79 guugg                                                                    5

<210> SEQ ID NO 80
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80 guugc                                                                    5

<210> SEQ ID NO 81
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81 gugug                                                                    5

<210> SEQ ID NO 82
<211> LENGTH: 5
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 82 guguu                                                                     5

<210> SEQ ID NO 83
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83 guguuuac                                                                  8

<210> SEQ ID NO 84
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84 guaggcac                                                                  8

<210> SEQ ID NO 85
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85 gucggcac                                                                  8

<210> SEQ ID NO 86
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86 cuaggcac                                                                  8

<210> SEQ ID NO 87
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87 cucggcac                                                                  8

<210> SEQ ID NO 88
<211> LENGTH: 13
<212> TYPE: RNA
<213> ORGANISM: Unknown
<220> FEATURE:
```

```
<223> OTHER INFORMATION: Description of Unknown:
      Kozak sequence

<400> SEQUENCE: 88
gccgccrcca ugg                                                          13

<210> SEQ ID NO 89
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89 auuua                                                                    5

<210> SEQ ID NO 90
<211> LENGTH: 500
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 1-500 nucleotides

<400> SEQUENCE: 90
aaaaaaaaaa aaaaaaaaaa aaaaaaaaaa aaaaaaaaaa aaaaaaaaaa aaaaaaaaaa       60
aaaaaaaaaa aaaaaaaaaa aaaaaaaaaa aaaaaaaaaa aaaaaaaaaa aaaaaaaaaa      120
aaaaaaaaaa aaaaaaaaaa aaaaaaaaaa aaaaaaaaaa aaaaaaaaaa aaaaaaaaaa      180
aaaaaaaaaa aaaaaaaaaa aaaaaaaaaa aaaaaaaaaa aaaaaaaaaa aaaaaaaaaa      240
aaaaaaaaaa aaaaaaaaaa aaaaaaaaaa aaaaaaaaaa aaaaaaaaaa aaaaaaaaaa      300
aaaaaaaaaa aaaaaaaaaa aaaaaaaaaa aaaaaaaaaa aaaaaaaaaa aaaaaaaaaa      360
aaaaaaaaaa aaaaaaaaaa aaaaaaaaaa aaaaaaaaaa aaaaaaaaaa aaaaaaaaaa      420
aaaaaaaaaa aaaaaaaaaa aaaaaaaaaa aaaaaaaaaa aaaaaaaaaa aaaaaaaaaa      480
aaaaaaaaaa aaaaaaaaaa                                                  500
```

ENHANCED IMMUNOGENICITY OF MRNA WITH CO-ENCODED ADJUVANT SEQUENCES

CROSS-REFERENCE TO RELATED APPLICATIONS

This application is a 35 U.S.C. § 111(a) Utility Application which claims benefit under 35 U.S.C. § 119(e) of U.S. Provisional Application Nos. 62/607,480 filed Dec. 19, 2017, 62/665,203 filed May 1, 2018, and 62/670,320 filed May 11, 2018, the contents of each of which are incorporated herein by reference in their entirety.

GOVERNMENT SUPPORT

This invention was made with Government Support under Contract No. HG008525 awarded by the National Institutes of Health (NIH). The Government has certain rights in the invention.

SEQUENCE LISTING

The instant application contains a Sequence Listing which has been filed electronically in ASCII format. Said ASCII copy, created on Jan. 8, 2019, is named 002806-091080USPT_SL.txt and is 31,196 bytes in size.

BACKGROUND OF THE INVENTION

Vertebrate immunity is divided into two arms: the adaptive immune system and the innate immune system, which work synergistically to mount an effective and sustained defense against pathogens. While the adaptive immune system takes days to produce a custom antibody response, the innate immune system initiates an immediate response that is more nonspecific in comparison and mounted in the first minutes and hours after pathogen exposure (Iwasaki and Medzhitov, 2015). A set of cellular sensors, known as "pattern-recognition receptors" (PRRs) are a major component of the innate immune system. PRRs are localized to a variety of subcellular compartments and can detect specific pathogen-associated molecular patterns (PAMPs) that are unique to pathogens and not found in the host. For example, members of the toll-like receptor family (TLRs) are localized to endosomal compartments, and each TLR subtype recognizes a distinct PAMP, such as single-stranded RNA (ssRNA) (recognized by TLR7/8) or double-stranded RNA (dsRNA) (recognized by TLR3), among others (Chow et al., 2015). Another family of PRRs, the RIG-I-like receptors (RLRs), are localized to the cytosol and detect dsRNA.

SUMMARY OF THE INVENTION

As demonstrated herein, an in vitro-transcribed (IVT) mRNA vaccine platform has been developed that combines a protein-coding sequence and an adjuvanting sequence within a single mRNA transcript that is more highly immunogenic than unmodified IVT mRNA. Accordingly, provided herein, in some aspects, are IVT mRNA vaccine platforms that combine a protein-coding sequence and an adjuvanting sequence within a single mRNA transcript that are more highly immunogenic than unmodified IVT mRNA.

Accordingly, one aspect described herein provides an in vitro-transcribed (IVT) RNA molecule comprising, a 5' cap structure, a coding region encoding an antigen polypeptide, an immunostimulatory RNA sequence, and a poly(A) tail.

In one embodiment, the IVT RNA molecule comprises, from 5' to 3', a 5' cap structure, a coding region encoding an antigen polypeptide, an immunostimulatory RNA sequence, and a poly(A) tail.

In one embodiment, the 5' cap structure comprises a synthetic cap structure selected from the group consisting of: 3'-O-Me-m7G(5')ppp(5')G; m7G(5')ppp(5')G; and G(5')ppp(5')G. In one embodiment of any aspect, the 5' cap structure is m7G(5')ppp(5')G.

Another aspect described herein provides an in vitro-transcribed (IVT) RNA molecule comprising, from 5' to 3': a m7G(5')ppp(5')G 5' cap; a coding region encoding influenza HA; SEQ ID NO:2; and a poly(A) tail.

In one embodiment of any aspect, the antigen polypeptide is influenza hemagglutinin (HA).

In one embodiment of any aspect, the IVT RNA molecule further comprises a linker sequence between the coding region encoding the antigen polypeptide and the immunostimulatory RNA sequence. In one embodiment of any aspect, the linker sequence is a poly A sequence. In one embodiment of any aspect, the linker sequence is AAAAA (SEQ ID NO: 6).

In one embodiment of any aspect, the immunostimulatory RNA sequence is SEQ ID NO: 2.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

The term "exogenous" as used herein refers to a nucleic acid (e.g., an IVT RNA molecule) that has been introduced by a process involving the hand of man into a biological system such as a cell or organism in which it is not normally found, or in which it is found in lower amounts. A factor is considered exogenous if it is introduced into an immediate precursor cell or a progeny cell that inherits the substance. In contrast, the term "endogenous" refers to a factor or expression product that is native to the biological system or cell (e.g., endogenous expression of a gene).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

BRIEF DESCRIPTION OF THE DRAWINGS

FIG. 6A. qRT-PCR analysis of IFNB1 mRNA in human prostate cancer cells (PC-3) transfected with 5 fmol IVT mRNA encoding eGFP-only or eGFP-DVG for 20 h. Results were normalized to ACTB mRNA, and fold induction is shown relative to IFNB1 mRNA in mock-transfected control cells, set as 1. FIG. 6B. Flow cytometry assessment of percentage of GFP positive PC-3 cells transfected as in FIG. 6A. FIG. 6C. Flow cytometry assessment of mean fluorescence intensity (MFI) of PC-3 cells transfected as in FIG. 6A. Data represent mean and SEM of n=3 biological replicates in FIG. 6A, n=2 biological replicates in FIGS. 6B and 6C. **P<0.01, (unpaired t-test).

FIG. 8A. qRT-PCR analysis of IFNB1 mRNA in mouse muscle myoblasts (C2C12) transfected with 100 fmol IVT mRNA encoding PR/8 HA-only or PR/8 HA-DVG for 20 h. Results were normalized to GAPDH mRNA, and fold induction is shown relative to IFNB1 mRNA in mock-transfected control cells, set as 1. FIG. 8B. qRT-PCR analysis of HA mRNA levels in cells transfected as in FIG. 8A. Data represent mean and SEM of n=3 biological replicates. PR/8 HA sequence was derived from the mouse-adapted influenza virus strain A/PR/8/34 (H1N1).

DETAILED DESCRIPTION

Figures 1A, 1B:
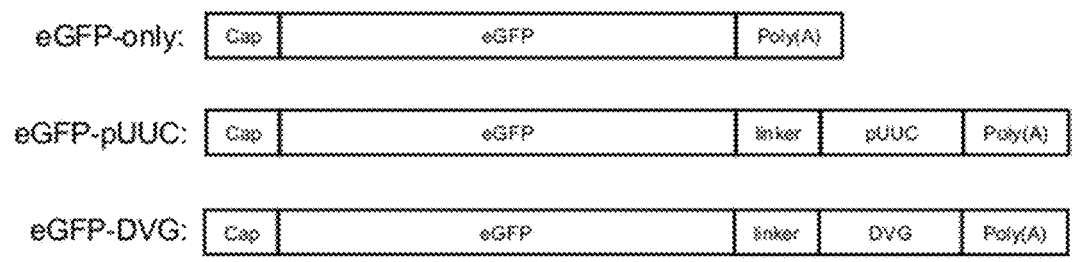
FIG. 1A. Nucleotide sequences of pUUC, a 104-nt RNA hepatitis C virus RNA motif (SEQ ID NO: 1), and DVG, a 45-nt Sendai virus RNA motif (SEQ ID NO: 2).
FIG. 1B. Schematic of IVT mRNA constructs used in this study. eGFP, enhanced green fluorescent protein; linker, 5-nt AAAAA sequence (SEQ ID NO: 6); pUUC, polyuridine sequence from hepatitis C virus as in (1A); DVG, defective viral genome sequence from Sendai virus as in (1B).

As described herein, a novel IVT mRNA vaccine platform has been developed having improved immunogenicity by combining antigen and adjuvant sequences in a single mRNA transcript. Surprisingly, as shown herein, incorporating short sequences that activate PRRs, like RIG-I, for example, within a much longer mRNA, results in the ability to trigger robust innate immune responses.

The compositions and methods described herein provide increased immunogenicity by expressing an antigen of interest in conjunction with an adjuvant sequence that helps to elicit a robust immune response to the expressed antigen, thereby mimicking typical pathogen activation of the immune response. Typically, upon detection of a PAMP, PRRs activate downstream signaling pathways that culminate in the upregulation of a diverse set of effector proteins, including secreted proinflammatory cytokines and type-I interferon (IFNs), which function to modulate gene expression, activate immune cells, and shape the adaptive immune response. As a safeguard against inappropriate immune responses, full activation of both innate and adaptive immune responses requires multiple signaling inputs that indicate the origin and pathogenicity of a detected substance. A vaccine that delivers inactivated virus or an isolated viral antigen does not stimulate as robust of an innate immune response compared to a live virus, and thus may not elicit potent antibody responses. This is because crucial components of the innate immune system are activated by signals that are only generated during viral replication and other parts of the viral life cycle. The use of adjuvants attempts to overcome these limitations that occur when using inactivated virus or an isolated viral antigen, by introducing substances, such as metal salts or oil emulsions, that promote additional immune activation, though molecular mechanisms underlying their adjuvant properties are not well understood (Coffman et al., 2010).

The discovery that innate immune PRRs, such as TLRs and RLRs, function as key regulators of antiviral cytokine signaling initially prompted the idea that PRR agonists could be useful as vaccine adjuvants (McKee and Marrack, 2017). For example, CpG-containing single-stranded oligonucleotides are sometimes co-administered with antigen to stimulate TLR9, which recognizes DNA in the endosome.

More recently, there has been interest in developing agonists of RLRs as vaccine adjuvants. Among the RLRs, retinoic acid-inducible gene I (RIG-I) and melanoma differentiation-associated protein 5 (MDA5) can sense viral RNA and initiate innate immune signaling. RIG-I preferentially senses short dsRNA in the cytosol, indicative of RNA virus infection, while MDA5 recognizes large web-like RNA aggregates produced during certain viral infections. In addition, a 5'-triphosphate or 5'-diphosphate moiety on the RNA, which is not present on most mature cellular RNAs, is thought to be important for RIG-I recognition (Chan and Gack, 2016). There have also been reports that RIG-I can be activated by much longer dsRNA (>200 bp) that do not bear a 5'-triphosphate end (Kolakofsky et al., 2012). Several agonists of RIG-I have been shown to act as virus vaccine adjuvants, including synthetic 5'-triphosphate dsRNA (Kulkarni et al., 2014) and a Sendai virus-derived RNA (Martinez-Gil et al., 2013), among others. One of the benefits of using immunostimulatory RNAs (isRNAs) as adjuvants compared to more traditional approaches is that the elicited immune response is broad and well-defined.

Recent advances in nucleic acid technology have also led to the emergence of mRNA as an alternative platform for vaccine development. For such applications, IVT mRNA encoding pathogen antigen or cancer antigen is delivered to target cells, where the cell's translation machinery produces the encoded protein, which subsequently elicits an antigen-specific immune response such as neutralizing antibodies. From a practical standpoint, IVT mRNA therapeutics are easy to manufacture and have a favorable safety profile compared to other vaccine strategies (Sahin et al., 2014). To function as effective vaccines, however, IVT mRNA therapeutics have two essential tasks: expressing antigen and eliciting a robust immune response to the expressed antigen. While mRNA stability and protein expression have been greatly improved in recent years, generating a balanced and effective immune response to IVT mRNA has remained a challenge.

However, in the context of IVT mRNA vaccines, although IVT mRNA possesses some intrinsic immunostimulatory activity, primarily through activation of the TLRs TLR7/8 and TLR3, this stimulation can be insufficient for generating sustained protective immunity (Devoldere et al., 2016). A variety of strategies have been employed to address this deficiency. For example, complexing IVT mRNA with a protamine carrier protein has been shown to enhance the immunogenicity of IVT mRNA, in part due to the enhanced activation of innate immune responses via TLR7 (Fotin-Mleczek et al., 2011; Petsch et al., 2012). The cytokine granulocyte/macrophage colony-stimulating factor (GM-CSF) has also been used as an adjuvant in conjunction with IVT mRNA to enhance T cell immunity (Carralot et al., 2004; Rittig et al., 2011). Moreover, some IVT mRNA delivery strategies, such as microinjection and electroporation, deposit IVT mRNA directly into the cytosol, bypassing activation of TLRs in endosomes via endocytosis of mRNA. Consequently, these delivery methods also require IVT mRNA formulations that include additional immunostimulatory components to achieve effective immunogenicity (Dewitte et al., 2014). The requirement for supplemental adjuvants in mRNA therapeutics necessitates the development of novel formulation and delivery methods and diminishes one of the major advantages of mRNA-based therapies: the ability to quickly produce large amounts of mRNA in a streamlined and controlled process. In addition, the precise mechanism of action of many currently used adjuvants are not well-understood and can lead to off-target effects and side effects. Because optimal immune responses are elicited when antigen and immunostimulatory factors are detected within the same cell (Iwasaki and Medzhitov, 2010), IVT mRNA vaccination strategies involving non-complexed adjuvant must deliver adjuvants in excess, which may have immunopathological effects.

In contrast, as described herein, the compositions and methods described herein differ from traditional vaccination methods in which the adjuvant is a separate component that is co-administered with the antigen (e.g., inactivated virus co-injected with alum) or complexed with the vaccine (e.g., mRNA complexed with protamine). Here, a novel IVT mRNA vaccine platform has been developed having improved immunogenicity by combining antigen and adjuvant sequences in a single mRNA transcript. Surprisingly, as shown herein, incorporating short sequences that activate PAMPs such as RIG-I, for example, within a much longer mRNA, results in the ability to trigger robust innate immune responses. As demonstrated herein, this isRNA-mediated enhancement of type-I IFN responses to the IVT mRNAs described herein is RIG-I dependent when the isRNA selected is for activating RIG-I. As also shown herein, isRNA-mediated enhancement of type-I IFN responses can occur in a variety of cell types, including human prostate cancer cells and mouse muscle cells, and results, in part, in enhanced MHC Class II expression, demonstrating the therapeutic implications of these technologies in enhancing antigen presentation. In addition, as demonstrated herein, the IVT mRNAs comprising isRNA can enhance type-I IFN responses to viral antigens, such as HA protein of influenza A virus. Accordingly, these data indicate broad efficacy of these IVT mRNAs as an integrated vaccine and adjuvant effective for raising an immune response to a wide range of target antigens.

As used herein, the term "IVT RNA" refers to a nucleic acid molecule encoding an antigen sequence to be expressed in a host for use as a vaccine, that has at least the following characteristics: (i) it can be generated by in vitro transcription and is not isolated from a cell; (ii) it is translatable in a mammalian (and preferably human) cell or subject to produce a polypeptide comprising an antigen; and (iii) it comprises an immunostimulatory sequence that activates a PAMP, such as RIG-I, and is distinct from the sequence encoding the antigen.

In regard to being generated by in vitro transcription, the IVT RNA molecule must be able to be generated by in vitro transcription of a DNA template. Methods for generating templates are well known to those of skill in the art using standard molecular cloning techniques. The transcribed, IVT RNA molecule can be modified further post-transcription, e.g., by adding a cap or other functional group. To be suitable for in vitro transcription, the nucleotides comprising the DNA template must be recognized as substrates by at least one RNA polymerase enzyme. Generally, RNA polymerase enzymes can tolerate a range of nucleoside base modifications, at least in part because the naturally occurring G, A, U, and C nucleoside bases differ from each other quite significantly. In addition, ribose and phosphate-modified nucleosides or nucleoside analogs are known in the art that permit transcription by RNA polymerases. In some embodiments of the aspects described herein, the RNA polymerase is a phage RNA polymerase. It is also contemplated that modified polymerases can be used to generate the IVT RNA molecules, as described herein. Thus, for example, a polymerase that tolerates or accepts a particular modified nucleoside as a substrate can be used to generate an IVT RNA molecule including that modified nucleoside.

The IVT RNA molecule used in the compositions and methods described herein must be translatable by the translation machinery of a eukaryotic, preferably mammalian, and more preferably, human cell, in vivo, to produce an antigen polypeptide. Translation generally requires at least a ribosome binding site, a methionine start codon, and an open reading frame encoding a polypeptide. Preferably, the IVT RNA molecule also comprises a 5' cap, a stop codon, and a polyA tail. In some embodiments, the IVT RNA molecule comprises a 5' cap, a stop codon, a Kozak sequence, and a polyA tail. In some embodiments, the IVT RNA molecule comprises a 5' untranslated region (5'-UTR, which can include sequence upstream of and in addition to a Kozak sequence (which encodes the initiator methionine)), a 3' untranslated region (3'-UTR), or both. In addition, where mRNAs in a eukaryotic cell are regulated by degradation, an IVT RNA molecule as described herein can be further modified to extend its half-life in the cell by incorporating one or more modifications to reduce the rate of RNA degradation (e.g., by increasing serum stability of an IVT RNA molecule). Various mRNA instability sequences are known that mediate degradation of mRNAs, and they frequently occur in the 3'-UTR of highly regulated naturally-occurring mRNAs. In one embodiment, the IVT RNA is designed to minimize the occurrence of such sequences, or to lack them altogether.

One can test an IVT RNA molecule for its ability to undergo translation and translation efficiency using an in vitro translation assay (e.g., a rabbit reticulocyte lysate assay, a reporter activity assay, or measurement of a radioactive label in the translated protein) and detecting the amount of the polypeptide produced using SDS-PAGE, Western blot, or immunochemistry assays etc.

Details regarding immunostimulatory RNA (isRNA) sequences for use with the compositions and methods described herein are provided in more detail below, including exemplary sequences. However, generally speaking, a key and novel feature of the IVT RNA molecules described herein is the presence of one or more isRNA sequences that activate one or more innate immune PRRs, such as RLRs and TLRs, thereby acting as an "adjuvanting" sequence. Thus, the IVT mRNA vaccine molecules described herein have improved and robust immunogenicity by incorporating short isRNA sequences that activate one or more PRRs, such as RIG-I, within a much longer mRNA transcript. While IVT mRNA tends to promote some degree of proinflammatory cytokine production, an IVT RNA molecule as described herein, which comprises an isRNA sequence as described herein, promotes the production of a proinflammatory cytokine to a greater extent than an RNA molecule that is identical but for the immunostimulatory RNA sequence. In this context, "to a greater extent" means at least 10% greater, at least 20% greater, at least 30% greater, at least 40% greater, at least 50% greater, at least 60% greater, at least 70% greater, at least 80% greater, at least 90% greater, at least 1-fold greater, at least 2-fold greater, at least 3-fold greater, or more, relative to an IVT RNA lacking the isRNA sequence.

Accordingly, provided herein, in some aspects are in vitro-transcribed (IVT) RNA molecules comprising, a 5' cap structure, a coding region encoding an antigen polypeptide, an immunostimulatory RNA sequence, and a poly(A) tail. In one embodiment, the IVT RNA molecule comprises, from 5' to 3', a 5' cap structure, a coding region encoding an antigen polypeptide, an isRNA sequence, and a poly(A) tail. In another embodiment, the IVT RNA comprises, from 5' to 3', a 5' cap, an isRNA sequence, a coding region encoding an antigen polypeptide, and a poly(A) tail. In another embodiment, the IVT RNA comprises, from 5' to 3', a 5' cap structure, a coding region encoding an antigen polypeptide, a poly(A) tail and an isRNA sequence.

A 5' cap is important for recognition and attachment of an mRNA to a ribosome to initiate translation. The 5' cap also protects the IVT RNA molecule from 5' exonuclease-mediated degradation. Thus, the 5' cap structure helps provide the IVT RNA molecule a longer half-life and increased efficiency of translation. A 5' cap structure, as described herein, necessarily excludes a 5'-triphosphate. Accordingly, in some embodiments, a 5' cap structure or 5' cap for use with IVT RNA molecules described herein can comprise a modified guanine nucleotide that is linked to the 5' end of an RNA molecule using a 5'-5' triphosphate linkage. As used herein, the term "5' cap" is also intended to encompass other 5' cap analogs including, e.g., 5' diguanosine cap, tetraphosphate cap analogs having a methylene-bis(phosphonate) moiety (see e.g., Rydzik, A M et al., (2009) Org Biomol Chem 7(22):4763-76), dinucleotide cap analogs having a phosphorothioate modification (see e.g., Kowalska, J. et al., (2008) RNA 14(6):1119-1131), cap analogs having a sulfur substitution for a non-bridging oxygen (see e.g., Grudzien-Nogalska, E. et al., (2007) RNA 13(10): 1745-1755), N7-benzylated dinucleoside tetraphosphate analogs (see e.g., Grudzien, E. et al., (2004) RNA 10(9):1479-1487), or anti-reverse cap analogs (see e.g., Jemielity, J. et al., (2003) RNA 9(9): 1108-1122 and Stepinski, J. et al., (2001) RNA 7(10): 1486-1495). In some embodiments, the IVT RNA molecule is capped with a modified ribonucleotide with the structure m7G(5')ppp(5')N(cap 0 structure) or a derivative thereof which can be incorporated during RNA synthesis, or can be enzymatically engineered after RNA transcription by using Vaccinia Virus Capping Enzyme (VCE, consisting of mRNA triphosphatase, guanylyl-transferase and guanine-7-methyltransferase), which catalyzes the construction of N7-monomethylated cap 0 structures. The Cap 0 structure is well-suited and effective to maintain the stability and translational efficacy of the IVT RNA vaccine. The 5' cap of the RNA vaccine can be further modified by a 2'-O-Methyltransferase. When applied to a Cap 0 structure, this generates a Cap 1 structure (m7 Gppp[m2'-O]N), which further increases translation efficacy. In some embodiments, the 5' cap structure is selected from 3'-O-Me-m7G(5')ppp(5')G, m7G(5')ppp(5')G, m7 Gppp[m2'-O]N, and G(5')ppp(5')G.

The antigen polypeptide encoded by the IVT RNA molecules described herein represents what these RNA vaccine molecules are targeted against. An "antigen," as used herein, refers to any molecule capable of being recognized by a T-cell antigen receptor or B-cell antigen receptor. The term broadly includes any type of molecule which is recognized by a host immune system as being foreign. Antigens generally include, but are not limited to cells, cell extracts, proteins, polypeptides, peptides, polysaccharides, polysaccharide conjugates, peptide and non-peptide mimics of polysaccharides and other molecules, small molecules, lipids, glycolipids, polysaccharides, carbohydrates, viruses and viral extracts, and multicellular organisms such as parasites, and allergens. However, in the context of RNA vaccines, as described herein, the antigen is a polypeptide or peptide encoded by the IVT RNA.

In various embodiments, the antigen encoded by the IVT RNA molecules is a microbial antigen, a cancer antigen, or an allergen. A "microbial antigen" as used herein is an antigen of or derived from a microorganism, and includes, but is not limited to, antigens from viruses, bacteria, parasites, and fungi. Such antigens include polypeptides and peptides expressed by such microbes and fragments or derivatives thereof.

Viruses are small infectious agents which generally contain a nucleic acid core and a protein coat, but are not independently living organisms. Viruses can also take the form of infectious nucleic acids lacking a protein. A virus cannot replicate in the absence of a living host cell. Viruses enter specific living cells either by endocytosis or direct injection of DNA and multiply, causing disease. The multiplied virus can then be released and infect additional cells. Some viruses are DNA-containing viruses and others are RNA-containing viruses.

Specific examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Hepaciviruses (hepatitis C viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxyiridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted); Norwalk and related viruses, and astroviruses.

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (coccus), straight-rod (*bacillus*) and curved or spiral rod (*vibrio, campylobacter*, spirillum, and spirochaete). Bacteria are also more commonly characterized based on their staining reactions into two classes of organisms, gram-positive and gram-negative. Gram refers to the method of staining which is commonly performed in microbiology labs. Gram-positive organisms retain the stain following the staining procedure and appear a deep violet color. Gram-negative organisms do not retain the stain but take up the counterstain and thus appear pink.

Infectious bacteria include, but are not limited to, gram negative and gram positive bacteria. Gram positive bacteria include, but are not limited to *Pasteurella* species, Staphylococci species, and *Streptococcus* species. Gram negative bacteria include, but are not limited to, *Escherichia coli, Pseudomonas* species, and *Salmonella* species. Specific examples of infectious bacteria include but are not limited to: *Helicobacter pylori, Borrelia burgdorferi, Legionella pneumophilia, Mycobacteria* sps (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia*, and *Actinomyces israelli*.

Parasites are organisms which depend upon other organisms in order to survive and thus must enter, or infect, another organism to continue their life cycle. The infected organism, i.e., the host, provides both nutrition and habitat to the parasite. Although in its broadest sense the term parasite can include all infectious agents (i.e., bacteria, viruses, fungi, protozoa and helminths), generally speaking, the term is used to refer solely to protozoa, helminths, and ectoparasitic arthropods (e.g., ticks, mites, etc.). Protozoa are single-celled organisms which can replicate both intracellularly and extracellularly, particularly in the blood, intestinal tract or the extracellular matrix of tissues. Helminths are multicellular organisms which almost always are extracellular (an exception being *Trichinella* spp.). Helminths normally require exit from a primary host and transmission into a secondary host in order to replicate. In contrast to these aforementioned classes, ectoparasitic arthropods form a parasitic relationship with the external surface of the host body.

Parasites include intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense* and *Schistosoma mansoni*.

Fungi are eukaryotic organisms, only a relative few of which cause infection in vertebrate mammals. Because fungi are eukaryotic organisms, they differ significantly from prokaryotic bacteria in size, structural organization, life cycle and mechanism of multiplication. Fungi are classified generally based on morphological features, modes of reproduction and culture characteristics. Although fungi can cause different types of disease in subjects, such as respiratory infection or allergies following inhalation of fungal antigens, fungal intoxication due to ingestion of toxic substances, such as *Amanita phalloides* toxin and phallotoxin produced by poisonous mushrooms and aflatoxins, produced by *aspergillus* species, not all fungi cause infectious disease.

Infectious fungi can cause systemic or superficial infections. Primary systemic infection can occur in normal healthy subjects, and opportunistic infections are most frequently found in immunocompromised subjects. The most common fungal agents causing primary systemic infection include *Blastomyces, Coccidioides*, and *Histoplasma*. Common fungi causing opportunistic infection in immunocompromised or immunosuppressed subjects include, but are not limited to, *Candida albicans, Cryptococcus neoformans*, and various *Aspergillus* species. Systemic fungal infections are invasive infections of the internal organs. The organism usually enters the body through the lungs, gastrointestinal tract, or intravenous catheters. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails.

Diseases associated with fungal infection include aspergillosis, blastomycosis, candidiasis, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, disseminated *Penicillium marneffei*, phaeohyphomycosis, rhinosporidioisis, sporotrichosis, and zygomycosis.

Other medically relevant microorganisms have been described extensively in the literature, e.g., see C. G. A Thomas, Medical Microbiology, Bailliere Tindall, Great Britain 1983, the entire contents of which is hereby incorporated by reference. Each of the foregoing lists is illustrative and is not intended to be limiting.

In some embodiments, the IVT RNA molecule is useful as a cancer vaccine, and the sequence encoding a polypeptide encodes a cancer antigen for use in eliciting an immune response against a cancer. As used herein, the terms "cancer antigen" and "tumor antigen" are used interchangeably to refer to a compound, such as a peptide, protein, or glycoprotein, which is associated with a tumor or cancer cell and which is capable of provoking an immune response when expressed on the surface of an antigen-presenting cell in the context of a major histocompatibility complex (MHC) molecule. Cancer antigens are differentially expressed by cancer cells and can thereby be exploited in order to target cancer cells. Cancer antigens are antigens which can stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation, and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses.

Non-limiting examples of tumor antigens include MAGE, MART-1/Melan-A, gp100, dipeptidyl peptidase IV (DP-PIV), adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-AL MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, p120ctn, gp100Pmel117, PRAME, NY-ESO-1, cdc27, adenomatous polyposis *coli* protein (APC), fodrin, Connexin 37, Ig-idiotype, p15, gp75, GM2 and GD2 gangliosides, viral products such as human papillomavirus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2. This list is not meant to be limiting. Amino acid sequences for these and other tumor antigens, and nucleic acid sequences that encode them, are known and available to those of ordinary skill in the art.

In some embodiments, the IVT RNA molecule acts as a vaccine against allergies and the sequence encoding a polypeptide encodes a allergen antigen for use in modifying an immune response against an allergen. An "allergen" as used herein is a molecule capable of provoking an immune response characterized by production of IgE. An allergen is also a substance that can induce an allergic or asthmatic response in a susceptible subject. Thus, as used herein, the term allergen means a specific type of antigen which can trigger an allergic response which is mediated by IgE antibody.

The list of allergens is enormous and can include pollens, insect venoms, animal dander dust, fungal spores and drugs (e.g., penicillin). Examples of natural animal and plant allergens include proteins specific to the following genuses: *Canis* (*Canis familiaris*); *Dermatophagoides* (e.g., *Dermatophagoides farinae*); *Felis* (*Felis domesticus*); *Ambrosia* (*Ambrosia artemisiifolia*); *Lolium* (e.g., *Lolium perenne* and *Lolium multiflorum*); *Cryptomeria* (*Cryptomeria japonica*); *Alternaria* (*Alternaria alternata*); *Alder; Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g., *Plantago lanceolata*); *Parietaria* (e.g., *Parietaria officinalis* and *Parietaria judaica*); *Blattella* (e.g., *Blattella germanica*); *Apis* (e.g., *Apis multiflorum*); *Cupressus* (e.g., *Cupressus sempervirens, Cupressus arizonica* and *Cupressus macrocarpa*); *Juniperus* (e.g., *Juniperus sabinoides, Juniperus virginiana, Juniperus communis*, and *Juniperus ashei*); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Festuca elatius*); *Poa* (e.g., *Poa pratensis* and *Poa compressa*); *Avena* (e.g., *Avena sativa*); *Holcus* (e.g., *Holcus lanatus*); *Anthoxanthum* (e.g., *Anthoxanthum odoratum*); *Arrhen-* atherum (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*).

An isRNA sequence for use with the compositions and methods described herein is designed and/or selected based on its ability to activate one or more PRRs, including RIG-I, PKR, MDA5, NALP3, TLR3, TLR7, and TLR8. By incorporating an isRNA sequence that activates one or more PRRs wherein introduction of the RNA molecule to a eukaryotic cell promotes a stronger antigen-specific immune response to the antigen polypeptide than introduction of an RNA molecule that differs from the RNA molecule only in lacking the immunostimulatory RNA sequence.

By activating these PRRs, such as through binding, the isRNA sequences for use with the IVT RNA molecules described herein promote the production of one or more proinflammatory cytokines when the IVT RNA molecule is introduced to or translated by a mammalian cell. Non-limiting examples of proinflammatory cytokines and chemokines include Type I interferons, such as IFN-α and IFN-β, Type II interferons, such as IFNγ, or Type III interferons, TNF-α, IL-6, IL-8, CXCL10, and CCR5, as well as one or more interferon stimulated genes or interferon signature genes (e.g., IFNα, IFNB1, IFIT, OAS1, PKR, RIGI, CCL5, RAP1A, CXCL10, IFIT1, CXCL11, MX1, RP11-167P23.2, HERC5, GALR3, IFIT3, IFIT2, RSAD2, and CDC20). For example, in some embodiments, introduction of an IVT RNA molecule to a eukaryotic cell promotes translation of the antigen polypeptide and production of one or more proinflammatory cytokines. Non-limiting examples of immunostimulatory RNA include ribosomal RNA (rRNA), transfer RNA (tRNA), messenger RNA (mRNA), and viral RNA (vRNA). An immunostimulatory RNA for use with the compositions and methods described herein can comprise a length of 5 to 30 nucleotides, 5 to 50 nucleotides, 5 to 100 nucleotides, 5 to 250 nucleotides, 5 to 500 nucleotides, 5 to 750 nucleotides, 5 to 1000 nucleotides, 5 to 5000 nucleotides, 500 to 5000 nucleotides, or 1000 to 5000 nucleotides.

The isRNA sequence for use with the compositions and methods described herein, is, in some embodiments, a sequence that activates RIG-I. Several RIG-I ligands have been described, as described in US20160008488, the contents of which are herein incorporated by reference in their entireties. For example, the structured HCV 5'-IRES and 3'-non translated regions. Both of these RNAs have been demonstrated to activate RIG-I (Sumpter et al, Supra, 2005; Saito T, Hirai R, Loo Y M, Owen D, Johnson C L, Sinha S C, Akira S, Fujita T, Gale, M. 2007. Proc. Natl. Acad. Sci. 104: 582-587). The HCV IRES is also an inhibitor of PKR (Vyas J, Elia A, Clemens M J. 2003 RNA 9: 858-870). Another RIG-I ligand is a 100 bp dsRNA region of the influenza genome. The influenza virus dsRNA is based on A/P R/8/34-H1N1 (PR8) and is a modification (to remove potential Pol III termination sequences) of the first 100 bp fragment of gene segment 3 (Lamb R A, Choppin P W. 1983. Annu Rev Biochem 52: 467-506)—this segment has potent in vivo immunostimulatory activity similar to natural influenza virus infection (Fang J, Bredow S, Taishi P, Majde J A, Krueger J M. 1999. J Med Virol 57: 198-203).

In some embodiments, short, triphosphorylated stem-loop RNA sequences (SLRs) can be used as isRNA sequences for RIG-I activation. Such SLRs are typically short, at 10 to 14 base pairs, and form a stem-loop. Non-limiting examples of such sequences can be found in "A minimal RNA ligand for potent RIG-I activation in living mice," Science Advances 21 Feb. 2018: Vol. 4, no. 2, e1701854, the contents of which are herein incorporated by reference in their entireties, and are shown below in Table 1. It is noted that in the context of an IVT mRNA as described herein, the isRNA for RIG-I activation would lack a 5' triphosphate, as it would be fused to the 3' side of the antigen-coding sequence.

TABLE 1

RNA ligands for RIG-I activation.

| | |
|---|---|
| ppp-NS<br>SEQ ID NO: 7 | 5'ppp-GAAGCAAUCUCCACUUACUAGAAA-OH3' |
| OH-SLR10<br>SEQ ID NO: 8 | 5'OH-GGACGUACGU$^U$ $_U$<br>  \|\|\|\|\|\|\|\|\|\|  <br>3'OH-CCUGCAUGCA$_G$ $^C$ |
| ppp-SLR10<br>SEQ ID NO: 9 | 5'ppp-GGACGUACGU$^U$ $_U$<br>  \|\|\|\|\|\|\|\|\|\|  <br>3'OH-CCUGCAUGCA$_G$ $^C$ |
| OH-SLR14<br>SEQ ID NO: 10 | 5'OH-GGAUCGAUCGAUCG$^U$ $_U$<br>  \|\|\|\|\|\|\|\|\|\|\|\|\|\|  <br>3'OH-CCCAGCUAGCUAGC$_G$ $^C$ |
| pp-SLR14<br>SEQ ID NO: 11 | 5'pp-GGAUCGAUCGAUCG$^U$ $_U$<br>  \|\|\|\|\|\|\|\|\|\|\|\|\|\|  <br>3'OH-CCUAGCUAGCUAGC$_G$ $^C$ |
| ppp-SLR14<br>SEQ ID NO: 12 | 5'ppp-GGAUCGAUCGAUCG$^U$ $_U$<br>  \|\|\|\|\|\|\|\|\|\|\|\|\|\|  <br>3'OH-CCUAGCUAGCUAGC$_G$ $^C$ |
| 19mer dS-ppp<br>SEQ ID NO:<br>13 & 14 | 5'ppp-GCAUGCGACCUCUGGUUGA-OH3'<br>\|\|\|\|\|\|\|\|\|\|\|\|\|\|\|\|\|\|\|<br>3'OH-CGUACGCUGCAGACAAACU-OH5' |
| 21mer dS-ppp<br>SEQ ID NO:<br>15 & 16 | 5'ppp-AACACACACACACACAGACACUUU-OH3'<br>\|\|\|\|\|\|\|\|\|\|\|\|\|\|\|\|\|\|\|\|\|<br>3'OH-UUGUGUGUGUGUGUGUGUGUG-OH5' |
| 23mer dS-ppp<br>SEQ ID NO:<br>17 & 18 | 5'ppp-AACACACACACACACACACACUUU-OH3'<br>\|\|\|\|\|\|\|\|\|\|\|\|\|\|\|\|\|\|\|\|\|\|\|<br>3'OH-UUGUGUGUGUGUGUGUGUGUGAA-OH5' |
| 24mer dS-OH<br>SEQ ID NO:<br>19 & 20 | 5'OH-GGACGUACGUUUCGCGACUGUAGA-OH3'<br>\|\|\|\|\|\|\|\|\|\|\|\|\|\|\|\|\|\|\|\|\|\|\|\|<br>3'OH-CCUGCAUGCAAAGCGCUGACAUCU-OH5' |
| 24mer dS-ppp<br>SEQ ID NO:<br>21 & 22 | 5'ppp-GGACGUACGUUUCGCGACUGUAGA-OH3'<br>\|\|\|\|\|\|\|\|\|\|\|\|\|\|\|\|\|\|\|\|\|\|\|\|<br>3'OH-CCUGCAUGCAAAGCGCUGACAUCU-OH5' |

In some embodiments the isRNA sequence that activates RIG-I comprises the pUUC sequence of SEQ ID NO: 1.

In some embodiments the isRNA sequence that activates RIG-I comprises the DVG sequence of SEQ ID NO: 2.

In some embodiments, an isRNA for use with the IVT molecules described herein comprises a nucleic acid having a motif of $G_lX_mG_n$ (SEQ ID NO: 3), wherein:

G is guanosine, uracil or an analogue of guanosine or uracil;

X is guanosine, uracil, adenosine, thymidine, cytosine or an analogue of the above-mentioned nucleotides; l is an integer from 1 to 40, wherein when l=1, G is guanosine or an analogue thereof, or when l>1 at least 50% of the nucleotides are guanosine or an analogue thereof;

m is an integer and is at least 3; wherein when m=3, X is uracil or an analogue thereof, or when m>3, at least 3 successive uracils or analogues of uracil occur;

n is an integer from 1 to 40, wherein when n=1 G is guanosine or an analogue thereof, or when n>1 at least 50% of the nucleotides are guanosine or an analogue thereof.

In some embodiments, an isRNA for use with the IVT molecules described herein comprises a nucleic acid having a motif of $C_lX_mC_n$ (SEQ ID NO: 4), wherein:

C is cytosine, uracil or an analogue of cytosine or uracil;

X is guanosine, uracil, adenosine, thymidine, cytosine or an analogue of the above-mentioned nucleotides;

l is an integer from 1 to 40, wherein when l=1 C is cytosine or an analogue thereof, or when l>1 at least 50% of the nucleotides are cytosine or an analogue thereof;

m is an integer and is at least 3; wherein when m=3 X is uracil or an analogue thereof, or when m>3 at least 3 successive uracils or analogues of uracil occur;

n is an integer from 1 to 40, wherein when n=1 C is cytosine or an analogue thereof, or when n>1 at least 50% of the nucleotides are cytosine or an analogue thereof.

The nucleic acids of SEQ ID NO: 3 or SEQ ID NO: 4 that can be used as an isRNA can be relatively short nucleic acid molecules with a typical length of approximately from 5 to 100 (but can also be longer than 100 nucleotides for specific embodiments, e.g., up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. Non-limiting examples of isRNA sequences comprising one or more of the motif sequences of SEQ ID NO: 3 and SEQ ID NO: 4 can be found in US20170266268 as SEQ ID NOs: 289-372, each of which is herein incorporated by reference in its entirety.

In some embodiments, an isRNA for use with the IVT molecules described herein comprises a nucleic acid having a formula of $N_uG_lX_mG_nN_v$ (SEQ ID NO: 5), wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40, wherein when l=1, G is guanosine (guanine) or an analogue thereof, or when l>1, at least 50% of these nucleotides (nucleosides) are guanosine (guanine) or an analogue thereof;

m is an integer and is at least 3; wherein when m=3, X is uridine (uracil) or an analogue thereof, and when m>3, at least 3 successive uridines (uracils) or analogues of uridine (uracil) occur;

n is an integer from 1 to 40, wherein when n=1, G is guanosine (guanine) or an analogue thereof, and when n>1, at least 50% of these nucleotides (nucleosides) are guanosine (guanine) or an analogue thereof, u, v may be independently from each other an integer from 0 to 50, preferably wherein when u=0, v≥1, or when v=0, u>1;

wherein the nucleic acid molecule of formula SEQ ID NO: 5 has a length of at least 50 nucleotides, preferably of at least 100 nucleotides, more preferably of at least 150 nucleotides, even more preferably of at least 200 nucleotides and most preferably of at least 250 nucleotides. Non-limiting examples of isRNA sequences falling within the formula of SEQ ID NO: 5 can be found in US20170266268 as SEQ ID NOs: 373-380, each of which is herein incorporated by reference in its entirety.

In some embodiments of the compositions and methods described herein, the isRNA sequence is a GU-rich single stranded sequence that activates TLR7, TLR8, or both TLR7 and TLR8.

In some embodiments, the isRNA sequence comprises the immunostimulatory RNA motif N-U-R1-R2 (SEQ ID NO: 23), where N is a ribonucleotide and N does not include a U; U is Uracil or a derivative thereof; R is a ribonucleotide wherein at least one of R1 and R2 is Adenosine (A) or Cytosine or derivatives thereof, and where R is not U unless N-U-R1-R2 includes at least two As. In some embodiments N is Adenosine or Cytosine (C) or derivatives thereof. In some embodiments, the isRNA sequence comprises more than one (i.e., 2, 3, or 4) immunostimulatory motifs of N-U-R1-R2 (SEQ ID NO: 23). The ORN does not include a TLR7/8 motif The ORN is preferably 4-100 in length and optionally includes at least one backbone modification. In some embodiments, N-U-R1-R2 (SEQ ID NO: 23-U-R1-R2 includes at least one G or C. In some embodiments the isRNA sequence is not ACCCAUCUAUUAUAUAACUC (SEQ ID NO: 24).

In other embodiments, the immunostimulatory RNA motif is separated from a 5' ribonucleotide by a non-nucleotide linker. In yet other embodiment, the immunostimulatory RNA motif is separated from a 3' ribonucleotide by a non-nucleotide linker. Optionally, the immunostimulatory RNA motif is separated from a 5' and 3' ribonucleotide by a non-nucleotide linker. In other embodiments, the immunostimulatory RNA motif includes at least one AU. In yet other embodiments, the immunostimulatory RNA motif includes at least one CU.

In some embodiments, the isRNA comprises one or more of the following TLR8 activating sequences: AUAGGCAC (SEQ ID NO: 25), GCCACCGAGCCGAAUAU AC (SEQ ID NO: 26), AUAUAUAUAUAUAUAUA UAU (SEQ ID NO: 27), UUAUUAUUAUUAUUAUU AUU (SEQ ID NO: 28), AAUAAUAAUAAUAAUAA UAA (SEQ ID NO: 29), AAAUAAAUAAAUAAAUAAAU (SEQ ID NO: 30), AAAAUAAAAUAAAAUAA AAU (SEQ ID NO: 31), CUACUACUACUACUACU ACU (SEQ ID NO: 32), UUAUUAU (SEQ ID NO: 33), UAUAUAU (SEQ ID NO: 34), CCGAGCCGCAUUACCC (SEQ ID NO: 35), CCGAGCCGAUUGAACC (SEQ ID NO: 36), CCGAGCCGAAUACCCC (SEQ ID NO: 37), CCGAGCCAUAUAUAUC (SEQ ID NO: 38), CCGAGCCGAUAUUACC (SEQ ID NO: 39), CCGAGCCGAAUCCCCC (SEQ ID NO: 40), CCGAGCCGCCUACCCC (SEQ ID NO: 41), CCGAGCCAUAUAUCCC (SEQ ID NO: 42), CCGAGCCGCUAUACCC (SEQ ID NO: 43), CCGAGCCGAAUAACCC (SEQ ID NO: 44), CCGAGCCGCUAUCCCC (SEQ ID NO: 45), CCGAGCCGAAGGUACC (SEQ ID NO: 46), CCGAGCCGAAGAUACC (SEQ ID NO: 47), CCGAGCCGAAUGUACC (SEQ ID NO: 48), CCGAGCCGCUAACCC (SEQ ID NO: 49), CCGAGCCGCAUAUCCC (SEQ ID NO: 50), CCGAGCCGAAGCUACC (SEQ ID NO: 51), CCGAGCCGCAUACCCC (SEQ ID NO: 52), CCGAGCCGCAUAACCC (SEQ ID NO: 53), CCGAGCGAAGGUGCC (SEQ ID NO: 54), CCGAGCCGCAUCCCCC (SEQ ID NO: 55), CCGAGCCGAAGCUGCC (SEQ ID NO: 56), CCGAGCCGCCGCCCC (SEQ ID NO: 57), CCGAGCCGAAGCUCCC (SEQ ID NO: 58), and CCGAGCCGAAGGCACC (SEQ ID NO: 59). Other examples of TLR8 activating sequences can be found in U.S. Pat. No. 7,662,949, the contents of which are herein incorporated by reference in their entireties.

In some embodiments, the isRNA comprises one or more of the following TLR7 and/or TLR8 activating sequences: 5'-C/U-U-G/U-U-3' (SEQ ID NO: 60), 5'-R-U-R-G-Y-3' (SEQ ID NO: 61), 5'-G-U-U-G-B-3'(SEQ ID NO: 62), 5'-G-U-G-U-G/U-3'(SEQ ID NO: 63), and 5'-G/C-U-A/C-G-G-C-A-C-3' (SEQ ID NO: 64), wherein C/U is cytosine (C) or uracil (U), G/U is guanine (G) or U, R is purine, Y is pyrimidine, B is U, G, or C, G/C is G or C, and A/C is adenine (A) or C.

In some embodiments, 5'-C/U-U-G/U-U-3' (SEQ ID NO: 60) is selected from CUGU (SEQ ID NO: 65), CUUU (SEQ ID NO: 66), UUGU (SEQ ID NO: 67), or UUUU (SEQ ID NO: 68).

In some embodiments, 5'-R-U-R-G-Y-3' (SEQ ID NO: 61) is selected from GUAGU (SEQ ID NO: 69), GUAGC (SEQ ID NO: 70), GUGGU (SEQ ID NO: 71), GUGGC (SEQ ID NO: 72), AUAGU (SEQ ID NO: 73), AUAGC (SEQ ID NO: 74), AUGGU (SEQ ID NO: 75), or AUGGC (SEQ ID NO: 76). In one embodiment the base sequence is GUAGUGU (SEQ ID NO: 77).

In some embodiments, 5'-G-U-U-G-B-3' (SEQ ID NO: 0 is selected from GUUGU (SEQ ID NO: 78), GUUGG (SEQ ID NO: 79), or GUUGC (SEQ ID NO: 80).

In some embodiments 5'-G-U-G-U-G/U-3' (SEQ ID NO: 63) is selected from GUGUG (SEQ ID NO: 81) or GUGUU (SEQ ID NO: 82). In one embodiment, the base sequence is GUGUUAC (SEQ ID NO: 83).

In some embodiments 5'-G/C-U-A/C-G-G-C-A-C-3' (SEQ ID NO: 64) is selected from GUAGGCAC (SEQ ID NO: 84), GUCGGCAC (SEQ ID NO: 85), CUAGGCAC (SEQ ID NO: 86), or CUCGGCAC (SEQ ID NO: 87).

The isRNA sequence for use with the compositions and methods described herein, is, in some embodiments, a sequence that activates TLR3. For example, the isRNA comprises a sequence permitting the formation of an intramolecular double-stranded region that binds and activates TLR3.

Viral isRNA sequences are also known that can be used with the compositions and methods described herein. For example, isRNA sequences can be used that are a viral immunostimulatory RNA sequence or a sequence at least 95% identical to a viral immunostimulatory RNA sequence. Non-limiting examples of viruses having immunostimulatory RNA sequences from which a viral immunostimulatory RNA sequence or sequence at least 95% identical to such sequence can be selected from include Sendai virus, Human Immunodeficiency Virus (HIV), and/or Hepatitis C virus (HCV), influenza A virus, measles virus, rabies virus, Ebola virus, and vesicular stomatitis virus (VSV).

The IVT RNA molecules described herein further comprise a "poly (A) tail," which refers to a 3' homopolymeric tail of adenine nucleotides, which can vary in length (e.g., at least 5 adenine nucleotides) and can be up to several hundred adenine nucleotides). The inclusion of a 3' poly(A) tail can protect the IVT RNA molecule from degradation in the cell, and also facilitates extra-nuclear localization to enhance translation efficiency. In some embodiments, the poly(A) tail comprises between 1 and 500 adenine nucleotides (SEQ ID NO: 90). In other embodiments the poly(A) tail comprises at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 225, at least 250, at least 275, at least 300, at least 325, at least 350, at least 375, at least 400, at least 425, at least 450, at least 475, at least 500 adenine nucleotides or more. In some embodiments, the poly(A) tail comprises between 1 and 150 adenine nucleotides. In some embodiments, the poly(A) tail comprises between 90 and 120 adenine nucleotides.

The IVT RNA molecules described herein can further comprise a linker sequence between the coding region encoding an antigen polypeptide and the immunostimulatory sequence. Typically, the linker sequence is 3' of the coding region encoding an antigen polypeptide and 5' of the immunostimulatory sequence. A non-limiting example of a linker for use with the IVT RNA molecules described herein is 5-nt AAAAA sequence (SEQ ID NO: 6). It is also contemplated that, in some embodiments, two or more isRNA sequences can be joined to an antigen-coding IVT mRNA sequence. In such instances, a linker sequence can also be included between the isRNA sequences.

Another modification for use with the IVT RNA molecules described herein, in some embodiments, involves linking, either chemically, or by encoding elements in the mRNA, one or more ligands, moieties or conjugates that enhance the activity, cellular distribution or cellular uptake of the RNA. Ligands can be particularly useful where, for example, an IVT RNA molecule is administered in vivo. Such moieties include but are not limited to lipid moieties such as a cholesterol moiety (Letsinger et al., Proc. Natl. Acid. Sci. USA, 1989, 86: 6553-6556, herein incorporated by reference in its entirety), cholic acid (Manoharan et al., Biorg. Med. Chem. Let., 1994, 4:1053-1060, herein incorporated by reference in its entirety), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770, each of which is herein incorporated by reference in its entirety), a thiocholesterol (Oberhauser et al., Nucl. Acids Res., 1992, 20:533-538, herein incorporated by reference in its entirety), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54, each of which is herein incorporated by reference in its entirety), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783, each of which is herein incorporated by reference in its entirety), a polyamine or a polyethylene glycol chain (Manoharan et al., Nucleosides & Nucleotides, 1995, 14:969-973, herein incorporated by reference in its entirety), or adamantane acetic acid (Manoharan et al., Tetrahedron Lett., 1995, 36:3651-3654, herein incorporated by reference in its entirety), a palmityl moiety (Mishra et al., Biochim. Biophys. Acta, 1995, 1264:229-237, herein incorporated by reference in its entirety), or an octadecylamine or hexylamino-carbonyloxycholesterol moiety (Crooke et al., J. Pharmacol. Exp. Ther., 1996, 277:923-937, herein incorporated by reference in its entirety).

The IVT RNA molecules described herein can further comprise a 5' and/or 3' untranslated region (UTR), separate from any naturally occurring or synthetic UTR sequence included within the isRNA sequence. Untranslated regions are regions of the RNA before the start codon (5') and after the stop codon (3'), and are therefore not translated by the translation machinery. Modification of an RNA molecule with one or more untranslated regions can improve the stability of an mRNA, since the untranslated regions can interfere with ribonucleases and other proteins involved in RNA degradation. In addition, modification of an IVT RNA molecule with a 5' and/or 3' untranslated region can enhance translational efficiency by binding proteins that alter ribosome binding to an mRNA. Modification of an IVT RNA molecule with a 3' UTR can be used to maintain a cytoplasmic localization of the RNA, permitting translation to occur in the cytoplasm of the cell. In some embodiments, the IVT RNA molecules described herein do not comprise a 5' or 3' UTR. In other embodiments, the IVT RNA molecules comprise either a 5' or 3' UTR. In other embodiments, the IVT RNA molecules described herein comprise both a 5' and a 3' UTR. For example, the 5' and/or 3' UTR can be selected from an mRNA known to have high stability in the cell (e.g., a murine alpha-globin 3' UTR).

In some embodiments, the IVT RNA molecules described herein further comprise a Kozak sequence. The "Kozak sequence" refers to a sequence on eukaryotic mRNA having the consensus (gcc)gccRccAUGG (SEQ ID NO: 88), where R is a purine (adenine or guanine) three bases upstream of the start codon (AUG), which is followed by another 'G'. The Kozak consensus sequence is recognized by the ribosome to initiate translation of a polypeptide. Typically, initiation occurs at the first AUG codon encountered by the translation machinery that is proximal to the 5' end of the transcript. However, in some cases, this AUG codon can be bypassed in a process called leaky scanning. The presence of a Kozak sequence near the AUG codon will strengthen that codon as the initiating site of translation, such that translation of the correct polypeptide occurs. Furthermore, addition of a Kozak sequence to an IVT RNA molecule will promote more efficient translation, even if there is no ambiguity regarding the start codon. Thus, in some embodiments, the IVT RNA molecules described herein further comprise a Kozak consensus sequence at the desired site for initiation of translation to produce the correct length polypeptide.

It is contemplated that one or more modifications to the IVT RNA molecules described herein permit greater stability of the IVT RNA molecule in a cell. To the extent that such modifications permit translation and do not interfere with the cell's innate immune or interferon response to the IVT RNA molecules, such modifications are specifically contemplated for use herein. Generally, the greater the stability of an IVT RNA molecule, the more protein can be produced from it. Typically, the presence of AU-rich regions in the 3' UTRs of mammalian mRNAs tend to destabilize transcripts, as cellular proteins are recruited to AU-rich regions to stimulate removal of the poly(A) tail of the transcript. Loss of a poly(A) tail of an IVT RNA molecule can result in increased RNA degradation. Thus, in some embodiments, IVT RNA molecules as described herein do not comprise an AU-rich region. In particular, it is preferred that the 3' UTR substantially lacks AUUUA (SEQ ID NO: 89) sequence elements.

In some embodiments, a ligand is used to alter the cellular uptake, intracellular targeting or half-life of an IVT RNA molecule into which it is incorporated. In some embodiments a ligand provides an enhanced affinity for a selected target, e.g., molecule, cell or cell type, intracellular compartment, e.g., mitochondria, cytoplasm, peroxisome, lysosome, as, e.g., compared to a composition absent such a ligand. Preferred ligands do not interfere with expression of a polypeptide from the IVT RNA molecules.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell targeting agent, (e.g., a lectin, glycoprotein, lipid or protein), or an antibody, that binds to a specified cell type such as a fibroblast cell. A targeting group can be, for example, a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, cholesterol, a steroid, bile acid, folate, vitamin B12, biotin, or an RGD peptide or RGD peptide mimetic, among others.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, amino, mercapto, PEG (e.g., PEG-40K), MPEG, [MPEG]2, polyamino, alkyl, substituted alkyl, radiolabeled markers, enzymes, haptens (e.g. biotin), and transport/absorption facilitators (e.g., aspirin, vitamin E, folic acid).

The ligand can be a substance, e.g., a drug, which can increase the uptake of the IVT RNA or a composition thereof into the cell, for example, by disrupting the cell's cytoskeleton, e.g., by disrupting the cell's microtubules, microfilaments, and/or intermediate filaments. The drug can be, for example, taxol, vincristine, vinblastine, cytochalasin, nocodazole, japlakinolide, latrunculin A, phalloidin, swinholide A, indanocine, or myoservin.

One exemplary ligand is a lipid or lipid-based molecule. A lipid or lipid-based ligand can (a) increase resistance to degradation, and/or (b) increase targeting or transport into a target cell or cell membrane. A lipid based ligand can be used to modulate, e.g., binding of the IVT RNA molecule composition to a target cell. In some embodiments, the lipid is N-[1-(2,3-Dioleoyloxy)propyl]-N,N,Ntrimethylammoniummethyl-sulfate (DOTAP).

In other embodiments, the ligand is a moiety, e.g., a vitamin, which is taken up by a host cell. Exemplary vitamins include vitamins A, E, and K. Other exemplary vitamins include B vitamin, e.g., folic acid, B12, riboflavin, biotin, pyridoxal or other vitamins or nutrients taken up, for example, by cancer cells. Also included are HSA and low density lipoprotein (LDL).

In other embodiments, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase. A "cell permeation peptide" is capable of permeating a cell, e.g., a mammalian cell, such as a human cell. For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In other embodiments, it is contemplated that an mRNA vaccine molecule including an antigen-coding sequence and an isRNA sequence as described herein can be chemically synthesized, rather than in vitro transcribed. Such an mRNA vaccine molecule can include any of the sequence elements, ligands, conjugates, modified nucleosides, linkers or other moieties, in any arrangement, as set out herein for an IVT mRNA vaccine molecule.

The IVT RNA molecules described herein are useful alone, or in combination, with other agents that act as further adjuvants or adjuvanting agents. An adjuvant as used herein refers to a substance other than the isRNA portion of the IVT RNA molecules described herein that enhances immune cell activation in response to an antigen, e.g., a humoral and/or cellular immune response. Adjuvants promote the accumulation and/or activation of accessory cells to enhance antigen-specific immune responses. Adjuvants are used to enhance the efficacy of vaccines, i.e., antigen-containing compositions used to induce protective immunity against the antigen.

Adjuvants, in general, include adjuvants that create a depot effect, immune-stimulating adjuvants, and adjuvants that create a depot effect and stimulate the immune system. An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720; AirLiquide, Paris, France); MF-59 (a squalene-in-water emulsion stabilized with Span 85 and Tween 80; Chiron Corporation, Emeryville, Calif.); and PROVAX (an oil-in-water emulsion containing a stabilizing detergent and a micelle-forming agent; IDEC Pharmaceuticals Corporation, San Diego, Calif.).

An immune-stimulating adjuvant is an adjuvant that causes activation of a cell of the immune system. It may, for instance, cause an immune cell to produce and secrete cytokines. This class of adjuvants includes but is not limited to saponins purified from the bark of the Q. saponaria tree, such as QS21 (a glycolipid that elutes in the 21 st peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). This class of adjuvants also includes CpG DNA.

Adjuvants that create a depot effect and stimulate the immune system are those compounds which have both of the above-identified functions. This class of adjuvants includes but is not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

In some embodiments, the IVT RNA molecule described herein and at least one other adjuvant are covalently linked to one another. Such combinations with other adjuvants can result in a synergistic immunostimulatory effect compared to the sum of effects of the IVT RNA molecule alone and the at least one other adjuvant alone. Additionally or alternatively, combinations with other adjuvants can result in an altered immunostimulatory profile compared to that of either the IVT RNA molecule alone or the at least one other adjuvant alone. For example, the combination can provide a more balanced form of Th1/Th2 immunostimulation in some embodiments, or provide a more skewed form of Th1/Th2 immunostimulation in other embodiments. Those skilled in the art will recognize how to select individual components to promote a desired type of immunostimulation, e.g., more balanced or more skewed with respect to Th1 and Th2 character.

In some embodiments, the IVT RNA molecule is conjugated with or co-administered with a cytokine acting as an adjuvant. Cytokines are soluble proteins and glycoproteins produced by many types of cells that mediate inflammatory and immune reactions. Cytokines mediate communication between cells of the immune system, acting locally as well as systemically to recruit cells and to regulate their function and proliferation. Categories of cytokines include mediators and regulators of innate immunity, mediators and regulators of adaptive immunity, and stimulators of hematopoiesis. Included among cytokines are interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, and interleukins 19-32 (IL-19-IL-32), among others), chemokines (e.g., IP-10, RANTES, MIP-1α, MIP-1β, MIP-3α, MCP-1, MCP-2, MCP-3, MCP-4, eotaxin, I-TAC, and BCA-1, among others), as well as other cytokines including type 1 interferons (e.g., IFN-α and IFN-β), type 2 interferon (e.g., IFN-γ), tumor necrosis factor-alpha (TNF-α), transforming growth factor-beta (TGF-β), and various colony stimulating factors (CSFs), including GM-CSF, G-CSF, and M-CSF.

In some embodiments, the IVT RNA molecule is conjugated with or co-administered with a lipopeptide acting as an adjuvant, such as Pam3Cys, a cationic polysaccharide such as chitosan, or a cationic peptide such as protamine.

Also provided herein, in some aspects, are methods of vaccinating a subject to produce an antigen-specific immune response to a target polypeptide, the method comprising introducing an effective amount of an IVT RNA molecule as described herein to a cell of the subject.

Provided herein, in some aspects, are methods of stimulating the production of a proinflammatory cytokine, the method comprising introducing any of the in vitro transcribed RNA molecules described herein to a mammalian cell.

As used herein, the term "effective amount" refers to that amount of a substance that is necessary or sufficient to bring about a desired biological effect. An effective amount can, but need not be, limited to an amount administered in a single administration. Combined with the teachings provided herein, by weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular IVT RNA molecule with or without another therapeutic agent, without necessitating undue experimentation.

Subject doses of the IVT RNA molecules described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day. For use in therapy, different doses may be necessary for treatment of a subject, depending on activity of the compound, manner of administration, purpose of the immunization (i.e., prophylactic or therapeutic), nature and severity of the disorder, age and body weight of the subject. The administration of a given dose can be carried out both by single administration in the form of an individual dose unit or else several smaller dose units. Multiple administration of doses at specific intervals of weeks or months apart is usual for boosting antigen-specific immune responses.

The pharmaceutical compositions containing IVT RNA molecules with or without other compounds can be administered by any suitable route for administering medications. A variety of administration routes are available. The particular mode selected depends upon the particular IVT RNA molecule selected, the particular condition being treated, and the dosage required for therapeutic efficacy. The methods described herein, generally speaking, can be practiced using any mode of administration that is medically acceptable, meaning any mode that produces effective levels of an immune response without causing clinically unacceptable adverse effects. Preferred modes of administration are discussed herein. For use in therapy, an effective amount of the IVT RNA molecules with or without other therapeutic agents can be administered to a subject by any mode that delivers the agent to the desired location, e.g., systemic vs. muscular, etc. Thus, administering the pharmaceutical compositions described herein can be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral.

The formulations of the IVT RNA molecules described herein are administered in pharmaceutically acceptable solutions, which can routinely contain pharmaceutically acceptable concentrations of salt, buffering agents, preservatives, compatible carriers, adjuvants, and optionally other therapeutic ingredients.

When it is desirable to deliver the IVT RNA molecules systemically, they can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the IVT RNA molecules in water-soluble form. Additionally, suspensions of the IVT RNA molecules can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described previously, the IVT RNA molecules can also be formulated as a depot preparation. Such long-acting formulations can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The IVT RNA molecules and optionally other therapeutics can be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

The IVT RNA molecules described herein can be formulated using one or more liposomes, lipoplexes, or lipid nanoparticles. Liposomes are artificially-prepared vesicles that are primarily composed of a lipid bilayer and can be used as a delivery vehicle for the administration of nutrients and pharmaceutical formulations. Liposomes can be of different sizes such as, but not limited to, a multilamellar vesicle (MLV), which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but need not necessarily comprise, opsonins or ligands in order to improve the attachment of liposomes or to activate events such as, but not limited to, endocytosis. Liposomes can contain a low or a high pH in order to improve the delivery of the pharmaceutical formulations, here, IVT RNAs.

In some embodiments, compositions comprising IVT RNA molecules can include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)[1,3]-dioxolane (DLin-KC2-DMA), and MC3 (US20100324120; herein incorporated by reference in its entirety) and liposomes such as, but not limited to, DOXIL from Janssen Biotech, Inc. (Horsham, Pa.).

In some embodiments, compositions comprising IVT RNA molecules can include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Bio-technol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; all of which are incorporated herein in their entireties). As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations can contain, but are not limited to, 48% cholesterol, 20% DSPC, 2% PEG-c-DMA, and 30% cationic lipid, where the cationic lipid can be 1,2-distearloxy-N,N-dimethylaminopropane (DSD-MA), DODMA, DLin-DMA, or 1,2-dilinolenyloxy-3-dimethylaminopropane (DLenDMA), as described by Heyes et al.

In some embodiments, the compositions comprising IVT RNA molecules are formulated in a lipid vesicle that have crosslinks between functionalized lipid bilayers.

In some embodiments, the compositions comprising IVT RNA molecules are formulated in a lipid-polycation complex. The formation of the lipid-polycation complex can be accomplished by methods known in the art and/or as described in U.S. Pub. No. 20120178702, herein incorporated by reference in its entirety. As a non-limiting example, the polycation can include a cationic peptide or a polypeptide such as, but not limited to, polylysine, polyornithine and/or polyarginine. In another embodiment, the polynucleotides, primary constructs and/or mmRNA can be formulated in a lipid-polycation complex which can further include a neutral lipid such as, but not limited to, cholesterol or dioleoyl phosphatidylethanolamine (DOPE).

The selection of the liposome formulation can be influenced by, for example, the selection of the cationic lipid component, the degree of cationic lipid saturation, the nature of the PEGylation, ratio of all components and biophysical parameters such as size. In some embodiments, the ratio of PEG in the LNP formulations can be increased or decreased and/or the carbon chain length of the PEG lipid can be modified from C14 to C18 to alter the pharmacokinetics and/or biodistribution of the LNP formulations. The cationic lipid can be selected from any lipid known in the art such as, but not limited to, DLin-MC3-DMA, DLin-DMA, C12-200 and DLin-KC2-DMA.

In some embodiments, the cationic lipid can be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893,302 and 7,404,969 and US Patent Publication No. US20100036115; each of which is herein incorporated by reference in their entireties. In another embodiment, the cationic lipid is selected from formula A described in International Publication Nos. WO2012040184, WO2011153120, WO2011149733, WO2011090965, WO2011043913, WO2011022460, WO2012061259, WO2012054365 and WO2012044638; each of which is herein incorporated by reference in their entireties. In other embodiments, the cationic lipid is selected from, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Patent Publication No. 0520100036115; each of which is herein incorporated by reference in their entireties. As non-limiting examples, the cationic lipid is selected from (20Z,23Z)—N,N-dimethylnonacosa-20,23-dien-10-amine, (17Z,20Z)—N,N-dimemylhexacosa-17,20-dien-9-amine, (1Z, 19Z)—N5N.about.dimethylpentacosa.about.16,19-dien-8-amine, (13Z,16Z)—N,N-dimethyldocosa-13J16-dien-5-amine, (12Z,15Z)—NJN-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z;19Z)—N,N-dimethylpentacosa-16,19-dien-6-amine, (22Z,25Z)—N,N-dimethylhentriaconta-22,25-dien-10-amine, (21Z,24Z)—N;N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—NJN-dimethyloctacosa-19,22-dien-7-amine, N,N-dimethylheptacosan-10-amine, (20Z,23Z)—N-ethyl-N-methylnonacosa-20J23-dien-10-amine, 1-[(11Z,14Z)-1-nonylicosa-11, 14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]heptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21.about. [(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyH-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropy 1]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propa-n-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy) methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy) methyl]ethyl}azetidine, (2S)-1-(hexyloxy)-N,N-dimethyl-3-[(9Z,12Z)-octadeca-9,12-dien-1-yloxy]pro-pan-2-amine, (2S)-1-(heptyloxy)-N,N-dimethyl-3-[(9Z,12Z)-octadeca-9,12-dien-1-yloxy]pr-opan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-am-ine (Compound 9); (2S)—N,N-dimethyl-1-[(6Z,9Z,12Z)-octadeca-6,9,12-trien-1-yloxy]-3-(octyl-oxy) propan-2-amine, (2S)-1-[(11Z,14Z)-icosa-11,14-dien-1-yloxy]-N,N-dimethyl-3-(pentyloxy)pro-pan-2-amine, (2S)-1-(hexyloxy)-3-[(11Z,14Z)-icosa-11,14-dien-1-yloxy]-N,N-dimethylprop-an-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)pr-opan-2-amine, (2S)-1-[(13Z,16Z)-docosa-13,16-dien-1-yloxy]-3-(hexyloxy)-N,N-dimethylpro-pan-2-amine, (2S)-1-[(13Z)-docos-13-en-1-yloxy]-3-(hexyloxy)-N,N-dimethylpropan-2-amin-e, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-di-en-1-yloxy]propan-2-amine, N,N-dimethyl-1-(octyloxy)-3-({8-[(1S,2S)-2-{[(1R,2R)-2-pentylcyclopropyl]-methyl}cyclopropyl]octyl}oxy)propan-2-amine, N,N-dimethyl-1-{[8-(2-oclylcyclopropyl)octyl]oxy}-3-(octyloxy)propan-2-am-ine and (11E,20Z,23Z)—N;N-dimethylnonacosa-11,20,2-trien-10-amine or a pharmaceutically acceptable salt or stereoisomer thereof.

In some embodiments, the LNP formulations of the compositions comprising IVT RNA molecules can contain PEG-c-DOMG between and including 1.5-3% lipid molar ratio. In some embodiments, the pharmaceutical compositions of the polynucleotides, primary constructs and/or mmRNA include at least one of the PEGylated lipids described in International Publication No. 2012099755, herein incorporated by reference. In some embodiments, the LNP formulation contains PEG-DMG 2000 (1,2-dimyristoyl-sn-glycero-3-phophoethanolamine-N-[methoxy(polyethylene glycol)-2000), a cationic lipid known in the art, and at least one other component. As a non-limiting example, the LNP formulation can contain PEG-DMG 2000, DLin-DMA, DSPC and cholesterol.

In some embodiments, the LNP formulation can be formulated by the methods described in International Publication Nos. WO2011127255 or WO2008103276, each of which is herein incorporated by reference in their entireties. As a non-limiting example, modified RNA can be encapsulated in LNP formulations as described in WO2011127255 and/or WO2008103276; each of which is herein incorporated by reference in their entireties.

In some embodiments, the LNP formulations comprise a polycationic composition. In some embodiments, the LNP formulations additionally comprise a permeability enhancer molecule. Non-limiting permeability enhancer molecules are described in US Patent Publication No. US20050222064; herein incorporated by reference in its entirety.

Lipid nanoparticle formulations for use with compositions comprising IVT RNA molecules can be improved by replacing the cationic lipid with a biodegradable cationic lipid, which is known as a rapidly eliminated lipid nanoparticle (reLNP). The rapid metabolism of the rapidly eliminated lipids can improve the tolerability and therapeutic index of the lipid nanoparticles. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain. The internal ester linkage can be located on either side of the saturated carbon.

In some embodiments, compositions comprising IVT RNA molecules are formulated as a lipoplex, such as, without limitation, the ATUPLEX system, the DACC system, the DBTC system and other siRNA-lipoplex technology from Silence Therapeutics (London, United Kingdom), STEMFECT from STEMGENT (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Mi-crovasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in their entireties).

In some embodiments, the compositions comprising IVT RNA molecules are formulated as a solid lipid nanoparticle. A solid lipid nanoparticle (SLN) can be spherical with an average diameter between 10 to 1000 nm. SLN possess a solid lipid core matrix that can solubilize lipophilic molecules and can be stabilized with surfactants and/or emulsifiers. The lipid nanoparticle can be a self-assembly lipid-polymer nanoparticle (see Zhang et al., ACS Nano, 2008, 2 (8), pp 1696-1702; herein incorporated by reference in its entirety).

Liposomes, lipoplexes, or lipid nanoparticles can be used to improve the efficacy of protein production as these formulations can increase cell transfection by the compositions comprising IVT RNA molecules; and/or increase the translation of encoded protein. One such example involves the use of lipid encapsulation to enable the effective systemic delivery of polyplex plasmid DNA (Heyes et al., Mol Ther. 2007 15:713-720; herein incorporated by ref-erence in its entirety). The liposomes, lipoplexes, or lipid nanoparticles can also be used to increase the stability of the compositions comprising IVT RNA molecules de-scribed herein.

The compositions comprising IVT RNA molecules described herein can, in some embodiments, be encapsulated into a lipid nanoparticle or a rapidly eliminating lipid nanoparticle, and the lipid nanoparticles or a rapidly eliminating lipid nanoparticle may then be encapsulated into a polymer, hydrogel and/or surgical seal-ant described herein and/or known in the art. As a non-limiting example, the polymer, hydrogel or surgical sealant may be PLGA, ethylene vinyl acetate (EVAc), poloxamer, GELSITE (Nano-therapeutics, Inc. Alachua, Fla.), HYLENEX (Halozyme Therapeutics, San Diego Calif.), surgical sealants such as fibrinogen polymers (Ethicon Inc. Cornelia, Ga.), TISSELL (Baxter International, Inc Deerfield, Ill.), PEG-based seal-ants, and COSEAL. (Baxter International, Inc Deerfield, Ill.).

Compositions comprising IVR RNA molecules can include formulations in which the IVT RNA is complexed or associated with one or more cationic polymers, including but not limited to polyethylene imine and cationic dendrim-ers.

The compositions comprising IVT RNA molecules can be encapsulated in a therapeutic nanoparticle. Therapeutic nanoparticles can be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, and U.S. Pat. No. 8,206,747; the contents of each of which are herein incorporated by reference in their entireties.

The nanoparticles used with the compositions comprising IVT RNA molecules described herein can comprise a poly-meric matrix. As a non-limiting example, the nanoparticle can comprise two or more polymers such as, but not limited to, polyethylenes, polycarbonates, polyanhydrides, polyhydroxyacids, polypro-pylfumerates, polycaprolactones, polyamides, polyacetals, polyethers, polyesters, poly(orthoesters), pol-ycyanoacrylates, polyvinyl alcohols, polyurethanes, polyphosphazenes, polyacrylates, polymeth-acry-lates, polycyanoacrylates, polyureas, polystyrenes, polyamines, polylysine, poly(ethylene imine), poly(serine ester), poly(L-lactide-co-L-lysine), poly(4-hydroxy-L-pro-line ester) or combinations thereof.

The nanoparticles used with the compositions comprising IVT RNA molecules described herein can comprise at least one acrylic polymer. Acrylic polymers include but are not limited to, acrylic acid, methacrylic acid, acrylic acid and methacrylic acid copolymers, methyl methacrylate copolymers, ethoxyethyl meth-acrylates, cyanoethyl methacrylate, amino alkyl methacrylate copolymer, poly(acrylic acid), poly(methacrylic acid), polycyanoacrylates and combinations thereof.

The nanoparticles used with the compositions comprising IVT RNA molecules described herein can comprise at least one cationic polymer described herein and/or known in the art.

The nanoparticles used with the compositions comprising IVT RNA molecules described herein can comprise at least one amine-containing polymer such as, but not limited to polylysine, polyethylene imine, poly(amidoamine) dendrim-ers and combinations thereof.

The nanoparticles used with the compositions comprising IVT RNA molecules can comprise at least one degradable polyester that can contain polycationic side chains. Degrade-able polyesters in-dude, but are not limited to, poly(serine ester), poly(L-lactide-co-L-lysine), poly(4-hydroxy-L-pro-line ester), and combinations thereof. In another embodi-ment, the degradable polyesters can include a PEG conju-gation to form a PEGylated polymer.

The compositions comprising IVT RNA molecules described herein can be encapsulated in, linked to and/or associated with synthetic nanocarriers. The synthetic nano-carriers can be formulated using methods known in the art and/or described herein. As a non-limiting example, the synthetic nanocarriers can be formulated by the methods described in International Pub Nos. WO2010005740, WO2010030763 and US Pub. Nos. US20110262491, US20100104645 and US20100087337, each of which is herein incorporated by refer-ence in their entireties. In some embodiments, the synthetic nanocarriers can contain reac-tive groups to release the compositions comprising IVT RNA molecules described herein (see International Pub. No. WO20120952552 and US Pub No. US20120171229, each of which is herein incorporated by reference in their entire-ties).

Other delivery systems can include time-release, delayed release or sustained release delivery systems. Such systems can avoid repeated administrations of the IVT RNA mol-ecules, increasing convenience to the subject and the phy-sician. Many types of release delivery systems are available and known to those of ordinary skill in the art. They include polymer base systems such as poly(lactide-glycolide), copo-lyoxalates, polycaprolactones, polyesteramides, polyorthoe-sters, polyhydroxybutyric acid, and polyanhydrides. Micro-capsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; pep-tide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery sys-tems can be used, some of which are adapted for implanta-tion.

The compositions and methods comprising the IVT RNA molecules described herein provide an enhanced immune response and activate one or more immune cells. As used herein, the term "activate an immune cell" refers to inducing an immune cell to enter an activated state that is associated with an immune response. The term "activate an immune cell" refers both to inducing and augmenting an immune response. As used herein, the term "immune response" refers to any aspect of an innate or adaptive immune response that reflects activation of an immune cell to proliferate, to perform an effector immune function, or to produce a gene product involved in an immune response. Gene products involved in an immune response can include secreted products (e.g., antibodies, cytokines, and chemokines) as well as intracellular and cell surface molecules characteristic of immune function (e.g., certain cluster of differentiation (CD) antigens, transcription factors, and gene transcripts). The term "immune response" can be applied to a single cell or to a population of cells. Production of cytokines and upregulation of cell surface markers of activation can be used to identify activation of the immune response by the IVT RNA molecules described herein and can be assessed by any of several methods well known in the art, including biological response assays, enzyme-linked immunosorbent assay (ELISA), intracellular fluorescence-activated cell sorting (FACS) analysis, and reverse transcriptase/polymerase chain reaction (RT-PCR).

A "subject" as used herein refers to a vertebrate animal. In preferred embodiments, the subject is a human, a non-human primate, or other mammal. In certain embodiments, the subject is a mouse, rat, guinea pig, rabbit, cat, dog, pig, sheep, goat, cow, or horse.

The compositions and methods described herein can be used, in some embodiments, alone or in conjunction with other agents and methods useful for the treatment of infection.

In some embodiments, the compositions and methods described herein can be used alone or in conjunction with other agents and methods useful for the treatment of cancer. In such embodiments, the compositions and methods are used for treating a subject having a cancer. In some such embodiments, both an effective amount of the composition comprising a suitable IVT RNA molecule and an anti-cancer therapy are used to treat the subject. A subject having a cancer is a subject that has detectable cancerous cells. The cancer may be a malignant or non-malignant cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma, biliary tract cancer; bladder cancer; bone cancer; brain and central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas, adenocarcinomas, and sarcomas.

Anti-cancer therapies for use with the compositions and methods described herein include cancer medicaments, radiation, and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Non-limiting examples of chemotherapeutic agents include methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

Immunotherapeutic agents include, but are not limited to, 3622W94, 4B5, ANA Ab, anti-FLK-2, anti-VEGF, ATRAGEN, AVASTIN (bevacizumab; Genentech), BABS, BEC2, BEXXAR (tositumomab; GlaxoSmithKline), C225, CAMPATH (alemtuzumab; Genzyme Corp.), CEACIDE, CMA 676, EMD-72000, ERBITUX (cetuximab; ImClone Systems, Inc.), Gliomab-H, GNI-250, HERCEPTIN (trastuzumab; Genentech), IDEC-Y2B8, ImmuRAIT-CEA, ior c5, ior egf.r3, ior t6, LDP-03, LymphoCide, MDX-11, MDX-22, MDX-210, MDX-220, MDX-260, MDX-447, MELIMMUNE-1, MELIMMUNE-2, Monopharm-C, NovoMAb-G2, Oncolym, OV103, Ovarex, Panorex, Pretarget, Quadramet, Ributaxin, RITUXAN (rituximab; Genentech), SMART 1D10 Ab, SMART ABL 364 Ab, SMART M195, TNT, and ZENAPAX (daclizumab; Roche).

In other aspects, provided herein are methods of producing an RNA vaccine molecule, the method comprising:

providing a DNA template comprising, in order, a bacteriophage promoter, a sequence encoding a vaccine target antigen, a linker, a sequence encoding an immunostimulatory RNA, and a poly(A) tail;

contacting the DNA template with an RNA polymerase that recognizes the bacteriophage promoter in the presence of ribonucleotides, a cap analog and reagents sufficient to permit transcription of the DNA template and transcript capping whereby an RNA vaccine molecule is produced.

The present invention is further illustrated by the following Examples, which in no way should be construed as further limiting.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Figure 2:
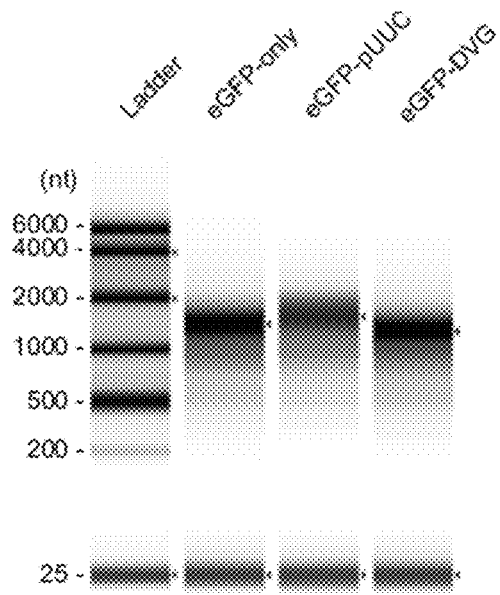
FIG. 2. Virtual gel image of in vitro transcribed RNA analyzed by Agilent 2100 Bioanalyzer.

To test whether an isRNA sequence incorporated within an mRNA transcript can enhance innate immune responses to IVT mRNA, we designed DNA constructs for in vitro transcription encoding a T7 promoter and enhanced green fluorescent protein (eGFP), followed by a 5-nucleotide spacer (AAAAA) (SEQ ID NO: 6) and an isRNA sequence, derived from either Sendai virus (SeV) or hepatitis C virus (HCV). The SeV sequence (called DVG here) encodes a 45-nt RNA motif derived from the defective viral genomes of SeV Cantell strain (Xu et al., 2015). The HCV sequence (called pUUC here) encodes a 104-nt RNA motif derived from the 3' untranslated region of the HCV genotype 1b genome (Saito et al., 2008; Schnell et al., 2012). In vitro-transcribed DVG and pUUC RNA with 5'triphosphate have been previously shown to potently activate RIG-I signaling and elicit strong antiviral cytokine responses. Based on structure prediction, the DVG and pUUC RNA motifs both possess double-stranded structures due to intramolecular base pairing, which may be responsible for their ability to activate RIG-I. We also generated a DNA construct encoding a T7 promoter sequence and eGFP only (eGFP-only). Using these constructs as templates, we produced mRNA by in vitro transcription using phage T7 RNA polymerase (FIGS. 1A-1B). IVT mRNAs were capped at the 5' end with a synthetic cap analog (ARCA), and a poly(A) tail was added to the 3' end. The concentration and integrity of the IVT mRNA was confirmed by Bioanalyzer (Agilent) (FIG. 2).

Figures 3A, 3B, 3C:
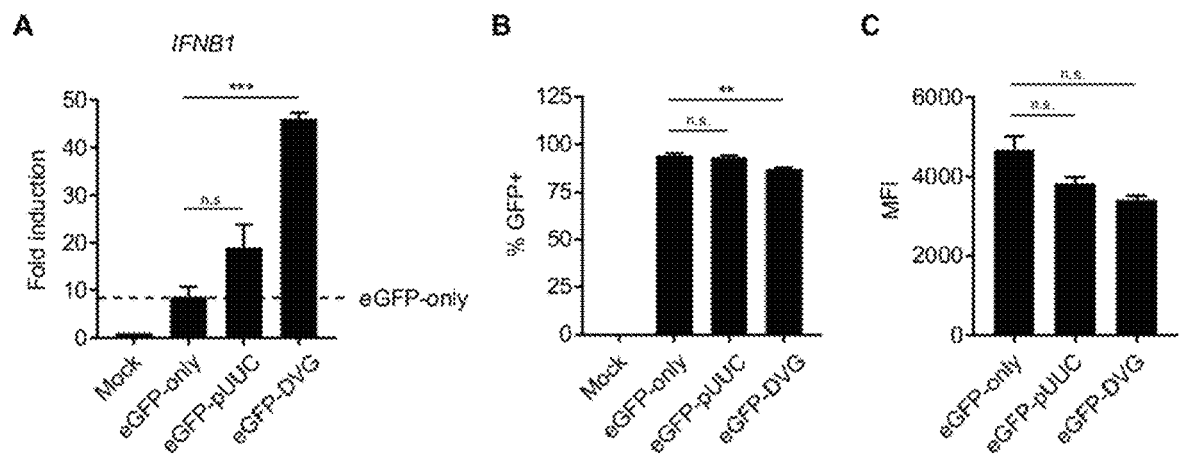
FIG. 3A. qRT-PCR analysis of IFNB1 mRNA in Huh7 cells transfected with 250 fmol mRNA encoding eGFP-only, eGFP-pUUC, or eGFP-DVG for 20 h. Results were normalized to ACTB mRNA, and fold induction is shown relative to IFNB1 mRNA in mock-transfected control cells, set as 1.
FIG. 3B. Flow cytometry assessment of percentage of GFP positive Huh7 cells transfected as in 3A.
FIG. 3C. Flow cytometry assessment of mean fluorescence intensity (MFI) of Huh7 cells transfected as in a. Data represent mean and SEM of n=3 biological replicates in 3A and 3C, n=2 biological replicates in b. P<0.01, *P<0.001 (unpaired t-test); n.s., not significant.

To compare the type-I IFN responses elicited by these mRNA constructs, we transfected equimolar amounts of each mRNA into Huh7 human hepatocyte-derived cellular carcinoma cells. Transfection of eGFP-only mRNA induced a ~9-fold increase in IFNB1 (a prototypical type-I IFN) expression compared to mock-transfected cells (FIG. 3A). Transfection of eGFP-DVG mRNA induced a 45-fold increase in IFNB1 expression—an approximately 5-fold enhancement over the IFNB1 levels elicited by eGFP-only mRNA. Although eGFP-pUUC mRNA transfection appeared to enhance IFNB1 levels compared to eGFP-only mRNA, the effect was not statistically significant, and further characterization of eGFP-pUUC is required (FIG. 3A). Flow cytometry analysis of mRNA-transfected cells showed that the proportion of eGFP-expressing cells was broadly similar amongst cells transfected with the different constructs (FIG. 3B) and that differences in mean fluorescence intensity were not significant (FIG. 3C). Taken together, these data show that the addition of the DVG isRNA sequence to IVT mRNA enhances the type-I IFN response to transfected IVT mRNA in vitro. This enhanced immunostimulatory activity seems to be specific to certain isRNAs, as an isRNA sequence derived from the HCV genome does not significantly affect the type-I IFN response to transfected mRNA. Appending a noncoding RNA sequence to the protein-coding region of an mRNA does not appear to have a major impact on mRNA uptake during transfection. Importantly, our data also suggest that the isRNA and its associated enhanced type-I IFN response do not significantly reduce expression of the co-encoded protein.

Figures 4A, 4B:
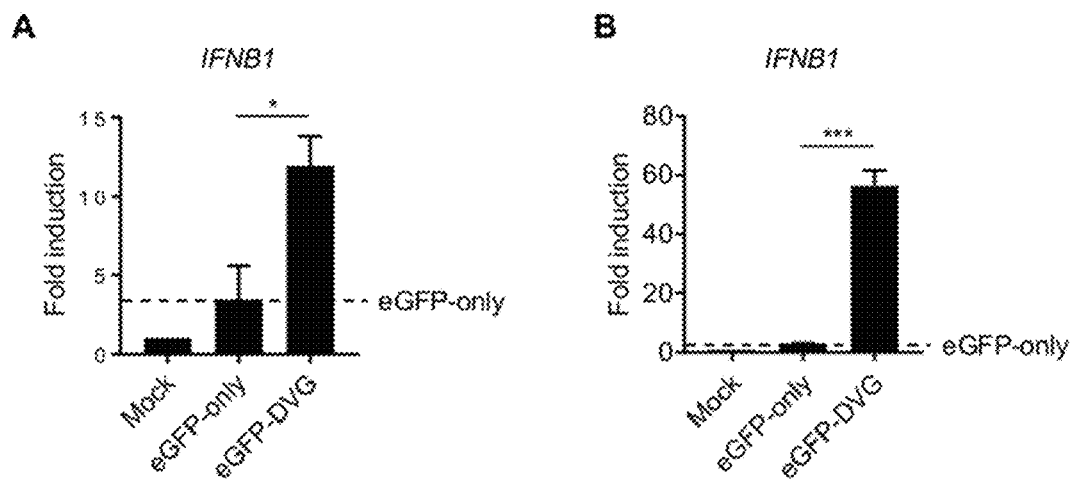
FIG. 4A. qRT-PCR analysis of IFNB1 mRNA in A549 cells transfected with 5 fmol eGFP-only or GFP-DVG mRNA for 20 h. Results were normalized to ACTB mRNA, and fold induction is shown relative to IFNB1 mRNA in mock-transfected control cells, set as 1.
FIG. 4B. qRT-PCR analysis of IFNB1 mRNA in NHLF cells transfected as in a. Data represent mean and SEM of n=3 biological replicates *P<0.05, ***P<0.001 (unpaired t-test)

The intrinsic immunostimulatory activity of IVT mRNA is generally attributed to its ability to activate TLRs. We hypothesized that even in cells that can mount robust innate immune responses to IVT mRNA via TLRs, eGFP-DVG mRNA would still elicit higher levels of type-I IFN than eGFP-only mRNA, since DVG RNA activates RIG-I, which signals through a different pathway than TLRs. It has previously been shown that transfecting respiratory cells with IVT mRNA induces a massive type-I IFN and proinflammatory cytokine response, which is thought to be mediated primarily by TLR3 (Andries et al., 2013). We observed that transfection with eGFP-DVG mRNA elicited significantly higher levels of IFNB1 expression compared to transfection with eGFP-only mRNA in both A549 human lung adenocarcinoma cells (FIG. 4A) and NHLF normal human lung fibroblasts (FIG. 4B). These data indicate that engaging multiple PRR pathways can enhance the innate immune response to IVT mRNA. The observation that incorporation of isRNA robustly activates type-I IFN induction even when the intrinsic immunostimulatory activity of mRNA does not significantly activate TLR signaling (FIG. 4B) indicates that mRNAisRNA can still elicit cytokine responses via RIG-I in cells that lack TLRs or have low TLR activity. In addition, these data demonstrate that IVT mRNA with co-encoded isRNA has enhanced immunostimulatory activity, including enhancing antigen presentation, in a potentially broad range of cell types, including cancer cells and muscle cells.

Figure 5:
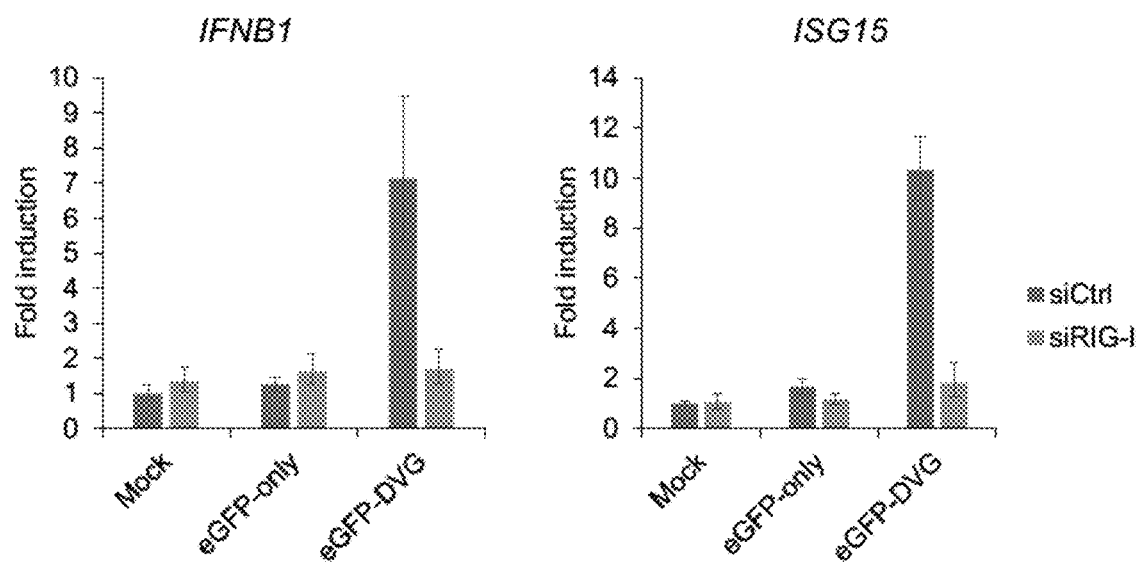
FIG. 5 demonstrates that isRNA-mediated enhancement of type-I IFN response to IVT mRNA is RIG-I dependent. qRT-PCR analysis of IFNB1 (left) and ISG15 (right) mRNA in Huh7 cells transfected with either non-targeting control siRNA (siCtrl), or siRNAs targeting RIG-I (siRIG-I) 30 h and then transfected with 100 fmol IVT mRNA encoding eGFP-only or eGFP-DVG for 20 h. Results were normalized to ACTB mRNA, and fold induction is shown relative to IFNB1 and ISG15 mRNA in mock-transfected control cells, set as 1. Data represent mean and SEM of n=3 biological replicates.

As shown herein in FIG. 5, isRNA-mediated enhancement of type-I IFN response to IVT mRNA is RIG-I dependent. qRT-PCR analysis of IFNB1 (left) and ISG15 (right) mRNA was performed in Huh7 cells transfected with either non-targeting control siRNA (siCtrl), or siRNAs targeting RIG-I (siRIG-I) 30 h and then transfected with 100 fmol IVT mRNA encoding eGFP-only or eGFP-DVG for 20 h.

Figures 6A, 6B, 6C:
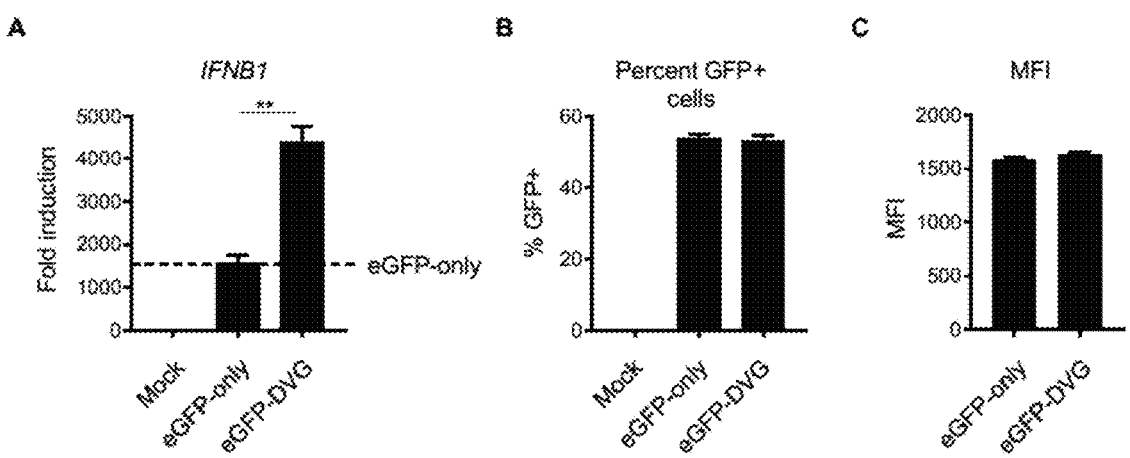
FIGS. 6A-6C demonstrate that isRNA enhances type-I IFN response to IVT mRNA in human prostate cancer cells.

Furthermore, as demonstrated in FIGS. 6A-6C, isRNA enhances type-I IFN response to IVT mRNA in human prostate cancer cells. qRT-PCR analysis of IFNB1 mRNA was performed in human prostate cancer cells (PC-3) transfected with 5 fmol IVT mRNA encoding eGFP-only or eGFP-DVG for 20 h. Results were normalized to ACTB mRNA, and fold induction is shown relative to IFNB1 mRNA in mock-transfected control cells, set as 1. Flow cytometry assessment of percentage of GFP positive PC-3 cells transfected as in FIG. 6A was performed. Flow cytometry assessment of mean fluorescence intensity (MFI) of PC-3 cells transfected as in FIG. 6A was performed.

Figure 7:
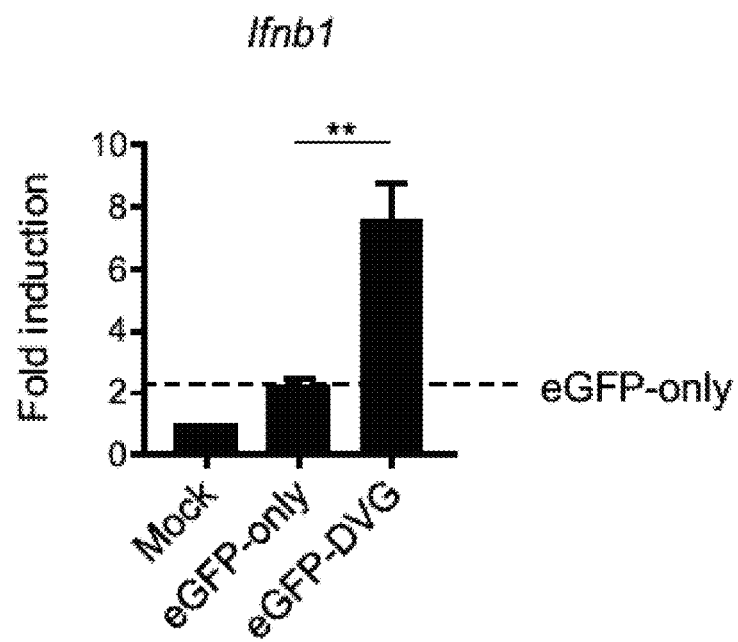
FIG. 7 demonstrates that isRNA enhances type-I IFN response to IVT mRNA in mouse muscle cells. qRT-PCR analysis of IFNB1 mRNA in mouse muscle myoblasts (C2C12) transfected with 100 fmol IVT mRNA encoding eGFP-only or eGFP-DVG for 20 h. Results were normalized to GAPDH mRNA, and fold induction is shown relative to IFNB1 mRNA in mock-transfected control cells, set as 1. Data represent mean and SEM of n=3 biological replicates **P<0.01, unpaired t-test.

As demonstrated in FIG. 7 isRNA enhances type-I IFN response to IVT mRNA in mouse muscle cells. qRT-PCR analysis of IFNB1 mRNA was performed in mouse muscle myoblasts (C2C12) transfected with 100 fmol IVT mRNA encoding eGFP-only or eGFP-DVG for 20 h. Results were normalized to GAPDH mRNA, and fold induction is shown relative to IFNB1 mRNA in mock-transfected control cells, set as 1.

Figures 8A, 8B:
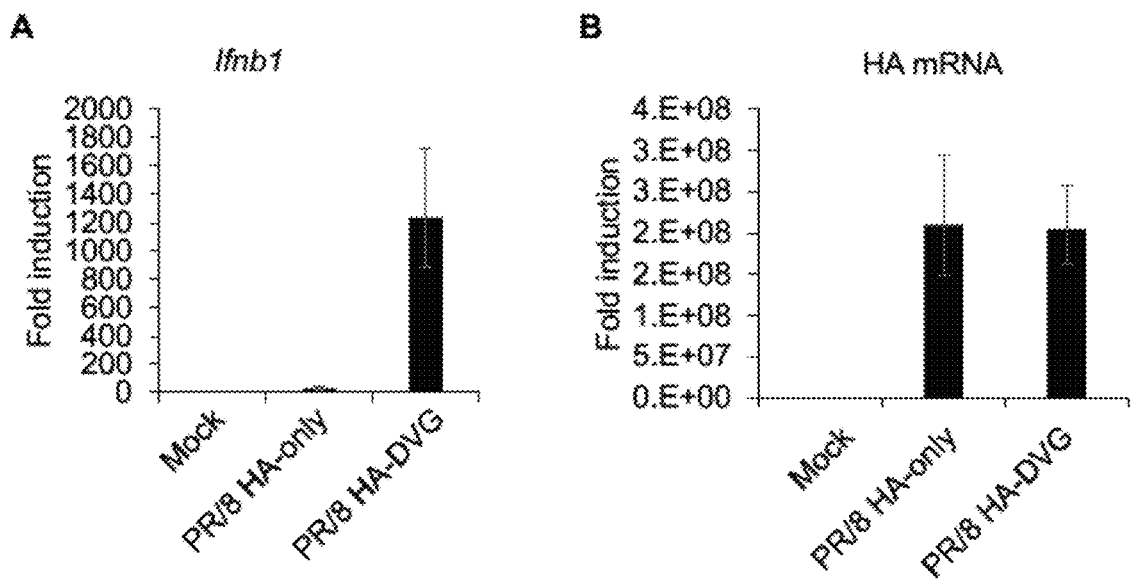
FIGS. 8A-8B demonstrate that isRNA enhances type-I IFN response to IVT mRNA encoding HA protein of influenza A virus.

In addition, FIGS. 8A-8B demonstrate that isRNA enhances type-I IFN responses to IVT mRNA encoding viral antigens, such as HA protein of influenza A virus. qRT-PCR analysis of IFNB1 mRNA was performed in mouse muscle myoblasts (C2C12) transfected with 100 fmol IVT mRNA encoding PR/8 HA-only or PR/8 HA-DVG for 20 h. Results were normalized to GAPDH mRNA, and fold induction is shown relative to IFNβ1 mRNA in mock-transfected control cells, set as 1. qRT-PCR analysis was performed of HA mRNA levels in cells transfected as in FIG. 8A.

Figure 9:
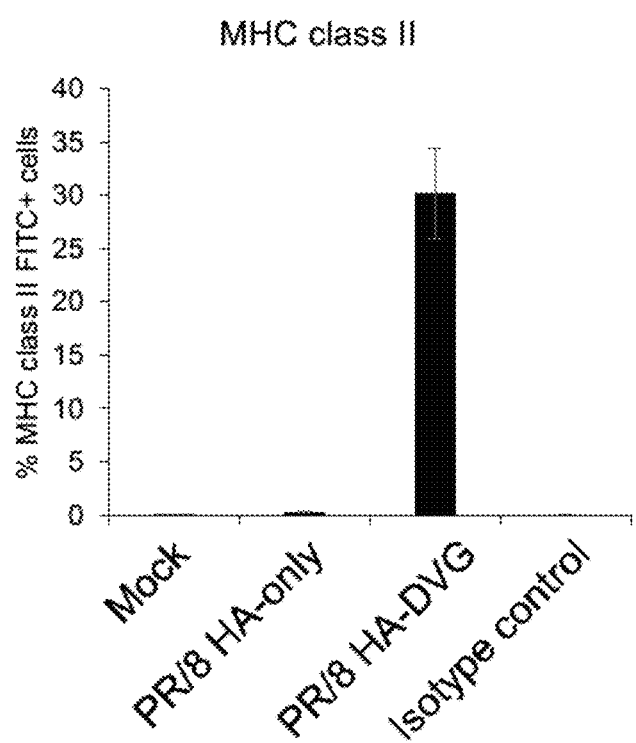
FIG. 9 demonstrates that isRNA enhances MHC class II expression in mouse muscle cells in response to transfected IVT mRNA. Flow cytometry analysis of percentage mouse muscle myoblasts (C2C12) expressing surface MHC class II 20 h post-transfection with 200 fmol IVT mRNA encoding PR/8 HA-only or PR/8 HA-DVG. Cells were stained with a FITC-conjugated antibody against MHC class II or an isotype control antibody. Data represent mean and SEM of n=3 biological replicates. PR/8 HA sequence was derived from the mouse-adapted influenza virus strain A/PR/8/34 (H1N1).

Furthermore, as demonstrated by FIG. 9, isRNA enhances a key marker of antigen presentation in a non-immune cell type, namely MHC class II expression in mouse muscle cells in response to transfected IVT mRNA. Flow cytometry analysis was performed to determine the percentage of mouse muscle myoblasts (C2C12) expressing MHC class II 20 h post-transfection with 200 fmol IVT mRNA encoding PR/8 HA-only or PR/8 HA-DVG. Cells were stained with a FITC-conjugated antibody against MHC class II or an isotype control antibody.

Accordingly, as described herein, we have engineered a modified IVT mRNA construct composed of an open reading frame (ORF) encoding eGFP, followed by a 5-nt AAAAA linker (SEQ ID NO: 6) and a 45-nt isRNA sequence derived from SeV defective viral genomes that elicits an enhanced innate immune response compared to unmodified IVT mRNA. In human hepatocytes, eGFP-DVG mRNA transfection elicited significantly higher type-I IFN expression levels compared to eGFP-only mRNA. Importantly, addition of the linker and isRNA sequence had minimal effects on cellular mRNA uptake during transfection and no significant effects on eGFP expression. An IVT mRNA construct encoding an isRNA sequence derived from the HCV genome showed weak or no enhanced immunostimulatory activity, indicating that isRNA sequences are differentially capable of triggering RIG-I activation when incorporated into an mRNA. Without wishing to be bound or limited by theory, we postulate that in the context of our mRNA constructs, double-stranded secondary structures formed by isRNA are the critical determinants of RIG-I activation. It remains to be tested whether other RIG-I agonists can also confer enhanced immunogenicity when incorporated into IVT mRNA, and several candidate RIG-I agonist isRNAs have been identified of both viral and host origin. Any isRNA sequences that have utility in this context can be easily incorporated into subsequent iterations of the constructs described herein.

Co-encoding a RIG-I agonist adjuvant within an IVT mRNA vaccine ("IVT mRNAisRNA") confers a number of advantages over unmodified IVT mRNA. While unmodified IVT mRNA primarily activates the TLR signaling pathway, our IVT mRNAisRNA construct activates both TLR and RLR signaling pathways for a response that more closely resembles the state of natural infection, in which a variety of PAMPs are present that activate different PRRs. Although the TLR and RLR pathways have some overlapping functions, such as the activation of common transcription factors, accumulating evidence suggests that TLR and RLR signaling are qualitatively different, and that the two pathways often play non-redundant roles in mounting an optimal immune response. For example, in monocyte-derived dendritic (moDC) cells, TLRs and RLRs have been shown to play distinct roles in antiviral cytokine responses, with TLR3 predominantly controlling the production of proinflammatory cytokines such as TNF and IL-6, and RLRs predominantly controlling the production of type-I IFN (Szabo et al., 2012). There are also examples of TLRs and RLRs acting in a temporally-distinct manner, for example during the bronchial epithelial cell response to rhinovirus infection, in which TLR3/7/8 signaling is activated early in infection while RLR signaling is induced late in infection (Slater et al., 2010). In all cases, both TLR and RLR signaling were required for full immune activation. The requirement for activation of multiple PRRs during pathogen infection, known as "coincidence detection," is thought to act as a safeguard against false detection (Tan et al., 2014). It has also been proposed that engagement of multiple PRRs prevents the overactivation of any individual pathway, thereby avoiding immunopathology (Nish and Medzhitov, 2011). Therefore, IVT mRNAisRNA activation of multiple PRR pathways may serve not only to augment immune responses but could also act as a natural brake to prevent excessive immune signaling. In addition, while TLRs are primarily expressed in immune cells, RIG-I is nearly ubiquitously expressed (Koyama et al., 2008). Therefore, incorporation of a RIG-I ligand within IVT mRNA may, without wishing to be bound or limited by theory, facilitate antigen presentation and immune activation by many cell types and potentially expand the range of tissues that could targeted by IVT mRNA vaccines.

In terms of formulation and manufacturing, encoding both antigen and adjuvant in a single IVT mRNA transcript greatly simplifies the production process. Generating IVT mRNAisRNA only involves modifying the template DNA, which is unlikely to significantly alter in vitro-transcription efficiency or other downstream production steps. Unlike the manufacturing process of IVT mRNA and adjuvant mixtures, which can result in heterogenous products (Phua et al., 2014), IVT mRNAisRNA production generates a clearly-defined and homogenous product. In addition, some formulations of IVT mRNA therapeutics utilize modified nucleotides to reduce the intrinsic immunostimulatory activity of mRNA (Kariko et al., 2011) Eliminating the immunogenicity of IVT mRNA is beneficial in protein replacement applications to optimize protein expression and to avoid generating inappropriate immune responses to the expressed protein, but the use of modified-nucleoside IVT mRNAs in vaccine applications requires innate immune activation. One strategy that has been used to restore immunogenicity to modified-nucleoside IVT mRNAs is complexing the mRNAs with a phospholipid agonist of TLR4 (Verbeke et al., 2017). Co-encoded isRNA sequences could potentially provide a much simpler solution for restoring immunogenicity in these "immunosilent" IVT mRNAs.

In addition to its antimicrobial activity, type-I IFN has also been shown to play an important role in counteracting other human pathologies, and there is a growing appreciation for the utility of targeting PRR-mediated type-I IFN signaling pathways in cancer immunotherapy (Parker et al., 2016; Wu et al., 2017). RLR signaling promotes anti-cancer immunity by activating immune responses and inducing tumor cell apoptosis, and RIG-I agonists have been shown to have potent antitumor activity. For example, administration of RIG-I agonists in mice has been shown to inhibit melanoma tumor growth (Poeck et al., 2008) and promote apoptosis of pancreatic cancer cells (Duewell et al., 2014). Moreover, RIG-I signaling has been shown to have antitumor activity that is independent of type-I IFN induction (Besch et al., 2009). IVT mRNA has been shown to be an effective platform for the development of cancer vaccines, but like viral vaccines, eliciting proper immune responses to tumor antigens remains a challenge (McNamara et al., 2015). Co-encoding RIG-I agonist sequences in IVT mRNA cancer vaccines may act to both enhance immunogenicity and directly promote tumor cell apoptosis.

REFERENCES

Andries, O., De Filette, M., De Smedt, S. C., Demeester, J., Van Poucke, M., Peelman, L., and Sanders, N. N. (2013). Innate immune response and programmed cell death following carrier-mediated delivery of unmodified mRNA to respiratory cells. J Control Release 167, 157-166.

Besch, R., Poeck, H., Hohenauer, T., Senft, D., Hacker, G., Berking, C., Hornung, V., Endres, S., Ruzicka, T., Rothenfusser, S., et al. (2009). Proapoptotic signaling induced by RIG-I and MDA-5 results in type I interferon-independent apoptosis in human melanoma cells. J Clin Invest 119, 2399-2411.

Carralot, J. P., Probst, J., Hoerr, I., Scheel, B., Teufel, R., Jung, G., Rammensee, H. G., and Pascolo, S. (2004). Polarization of immunity induced by direct injection of naked sequence-stabilized mRNA vaccines. Cell Mol Life Sci 61, 2418-2424.

Chan, Y. K., and Gack, M. U. (2016). Viral evasion of intracellular DNA and RNA sensing. Nat Rev Microbiol 14, 360-373.

Chow, J., Franz, K. M., and Kagan, J. C. (2015). PRRs are watching you: Localization of innate sensing and signaling regulators. Virology 479-480, 104-109.

Coffman, R. L., Sher, A., and Seder, R. A. (2010). Vaccine adjuvants: putting innate immunity to work. Immunity 33, 492-503.

Devoldere, J., Dewitte, H., De Smedt, S. C., and Remaut, K. (2016). Evading innate immunity in nonviral mRNA delivery: don't shoot the messenger. Drug Discov Today 21, 11-25.

Dewitte, H., Van Lint, S., Heirman, C., Thielemans, K., De Smedt, S. C., Breckpot, K., and Lentacker, I. (2014). The potential of antigen and TriMix sonoporation using mRNA-loaded microbubbles for ultrasound-triggered cancer immunotherapy. J Control Release 194, 28-36.

Duewell, P., Steger, A., Lohr, H., Bourhis, H., Hoelz, H., Kirchleitner, S. V., Stieg, M. R., Grassmann, S., Kobold, S., Siveke, J. T., et al. (2014). RIG-I-like helicases induce immunogenic cell death of pancreatic cancer cells and sensitize tumors toward killing by CD8(+) T cells. Cell Death Differ 21, 1825-1837.

Fotin-Mleczek, M., Duchardt, K. M., Lorenz, C., Pfeiffer, R., Ojkic-Zrna, S., Probst, J., and Kallen, K. J. (2011). Messenger RNA-based vaccines with dual activity induce balanced TLR-7 dependent adaptive immune responses and provide antitumor activity. J Immunother 34, 1-15.

Iwasaki, A., and Medzhitov, R. (2010). Regulation of adaptive immunity by the innate immune system. Science 327, 291-295.

Iwasaki, A., and Medzhitov, R. (2015). Control of adaptive immunity by the innate immune system. Nat Immunol 16, 343-353.

Kariko, K., Muramatsu, H., Ludwig, J., and Weissman, D. (2011). Generating the optimal mRNA for therapy: HPLC purification eliminates immune activation and improves translation of nucleoside-modified, protein-encoding mRNA. Nucleic Acids Res 39, e142.

Kolakofsky, D., Kowalinski, E., and Cusack, S. (2012). A structure-based model of RIG-I activation. RNA 18, 2118-2127.

Koyama, S., Ishii, K. J., Coban, C., and Akira, S. (2008). Innate immune response to viral infection. Cytokine 43, 336-341.

Kulkarni, R. R., Rasheed, M. A., Bhaumik, S. K., Ranjan, P., Cao, W., Davis, C., Marisetti, K., Thomas, S., Gangappa, S., Sambhara, S., et al. (2014). Activation of the RIG-I pathway during influenza vaccination enhances the germinal center reaction, promotes T follicular helper cell induction, and provides a dose-sparing effect and protective immunity. J Virol 88, 13990-14001.

Martinez-Gil, L., Goff, P. H., Hai, R., Garcia-Sastre, A., Shaw, M. L., and Palese, P. (2013). A Sendai virus-derived RNA agonist of RIG-I as a virus vaccine adjuvant. J Virol 87, 1290-1300.

McKee, A. S., and Marrack, P. (2017). Old and new adjuvants. Curr Opin Immunol 47, 44-51.

McNamara, M. A., Nair, S. K., and Holl, E. K. (2015). RNA-Based Vaccines in Cancer Immunotherapy. J Immunol Res 2015, 794528.

Nish, S., and Medzhitov, R. (2011). Host defense pathways: role of redundancy and compensation in infectious disease phenotypes. Immunity 34, 629-636.

Parker, B. S., Rautela, J., and Hertzog, P. J. (2016). Antitumour actions of interferons: implications for cancer therapy. Nat Rev Cancer 16, 131-144.

Petsch, B., Schnee, M., Vogel, A. B., Lange, E., Hoffmann, B., Voss, D., Schlake, T., Thess, A., Kallen, K. J., Stitz, L., et al. (2012). Protective efficacy of in vitro synthesized, specific mRNA vaccines against influenza A virus infection. Nat Biotechnol 30, 1210-1216.

Phua, K. K., Nair, S. K., and Leong, K. W. (2014). Messenger RNA (mRNA) nanoparticle tumour vaccination. Nanoscale 6, 7715-7729.

Poeck, H., Besch, R., Maihoefer, C., Renn, M., Tormo, D., Morskaya, S. S., Kirschnek, S., Gaffal, E., Landsberg, J., Hellmuth, J., et al. (2008). 5'-Triphosphate-siRNA: turning gene silencing and Rig-I activation against melanoma. Nat Med 14, 1256-1263.

Rittig, S. M., Haentschel, M., Weimer, K. J., Heine, A., Muller, M. R., Brugger, W., Horger, M. S., Maksimovic, O., Stenzl, A., Hoerr, I., et al. (2011). Intradermal vaccinations with RNA coding for TAA generate CD8+ and CD4+ immune responses and induce clinical benefit in vaccinated patients. Mol Ther 19, 990-999.

Sahin, U., Kariko, K., and Tureci, O. (2014). mRNA-based therapeutics—developing a new class of drugs. Nat Rev Drug Discov 13, 759-780.

Saito, T., Owen, D. M., Jiang, F., Marcotrigiano, J., and Gale, M., Jr. (2008). Innate immunity induced by composition-dependent RIG-I recognition of hepatitis C virus RNA. Nature 454, 523-527.

Schnell, G., Loo, Y. M., Marcotrigiano, J., and Gale, M., Jr. (2012). Uridine composition of the poly-U/UC tract of HCV RNA defines non-self recognition by RIG-I. PLoS Pathog 8, e1002839.

Slater, L., Bartlett, N. W., Haas, J. J., Zhu, J., Message, S. D., Walton, R. P., Sykes, A., Dandaleh, S., Clarke, D. L., Belvisi, M. G., et al. (2010). Co-ordinated role of TLR3, RIG-I and MDA5 in the innate response to rhinovirus in bronchial epithelium. PLoS Pathog 6, e1001178.

Szabo, A., Bene, K., Gogolak, P., Rethi, B., Lanyi, A., Jankovich, I., Derso, B., and Rajnavolgyi, E. (2012). RLR-mediated production of interferon-beta by a human dendritic cell subset and its role in virus-specific immunity. J Leukoc Biol 92, 159-169.

Tan, R. S., Ho, B., Leung, B. P., and Ding, J. L. (2014). TLR cross-talk confers specificity to innate immunity. Int Rev Immunol 33, 443-453.

Verbeke, R., Lentacker, I., Wayteck, L., Breckpot, K., Van Bockstal, M., Descamps, B., Vanhove, C., De Smedt, S. C., and Dewitte, H. (2017). Co-delivery of nucleoside-modified mRNA and TLR agonists for cancer immunotherapy: Restoring the immunogenicity of immunosilent mRNA. J Control Release 266, 287-300.

Wu, Y., Wu, X., Wu, L., Wang, X., and Liu, Z. (2017). The anticancer functions of RIG-I-like receptors, RIG-I and MDA5, and their applications in cancer therapy. Transl Res.

Xu, J., Mercado-Lopez, X., Grier, J. T., Kim, W. K., Chun, L. F., Irvine, E. B., Del Toro Duany, Y., Kell, A., Hur, S., Gale, M., Jr., et al. (2015). Identification of a Natural Viral RNA Motif That Optimizes Sensing of Viral RNA by RIG-I. MBio 6, e01265-01215.

What is claimed:

1. An in vitro-transcribed (IVT) RNA molecule comprising, a 5' cap structure, a coding region encoding an antigen polypeptide, an immunostimulatory RNA sequence that activates RIG-I, and a poly(A) tail.

2. The IVT RNA molecule of claim 1, comprising, from 5' to 3', a 5' cap structure, a coding region encoding an antigen polypeptide, an immunostimulatory RNA sequence that activates RIG-I, and a poly(A) tail.

3. The IVT RNA molecule of claim 1, wherein the 5' cap structure comprises a synthetic cap structure selected from the group consisting of: 3'-O-Me-m7G(5')ppp(5')G; m7G(5')ppp(5')G; and G(5')ppp(5')G.

4. The IVT RNA molecule of claim 3, wherein the 5' cap structure is m7G(5')ppp(5')G.

5. The IVT RNA molecule of claim 1, wherein the antigen polypeptide is influenza hemagglutinin (HA).

6. The IVT RNA molecule of claim 1, further comprising a linker sequence between the coding region encoding the antigen polypeptide and the immunostimulatory RNA sequence that activates RIG-I.

7. The IVT RNA molecule of claim 6, wherein the linker sequence is a poly A sequence.

8. The IVT RNA molecule of claim 7, wherein the linker sequence is AAAAA (SEQ ID NO: 6).

9. The IVT RNA molecule of claim 1, wherein the immunostimulatory RNA sequence that activates RIG-I is SEQ ID NO: 2.

10. An in vitro-transcribed (IVT) RNA molecule comprising, from 5' to 3':

a m7G(5')ppp(5')G 5' cap, a coding region encoding influenza HA,

SEQ ID NO:2, and a poly(A) tail.

11. The IVT RNA molecule of claim 10, further comprising a linker sequence between the coding region encoding the antigen polypeptide and the immunostimulatory RNA sequence that activates RIG-I.

12. The IVT RNA molecule of claim 11, wherein the linker sequence is a poly A sequence.

13. The IVT RNA molecule of claim 12, wherein the linker sequence is AAAAA (SEQ ID NO: 6).

* * * * *